(12) United States Patent  (10) Patent No.: US 7,729,472 B2
Scherch et al.  (45) Date of Patent: *Jun. 1, 2010

(54) SYSTEM FOR ANALYZING THE GEOMETRY OF A RADIATION TREATMENT APPARATUS, SOFTWARE AND RELATED METHODS

(75) Inventors: John David Scherch, Pittsburgh, PA (US); Edward Charles Smetak, Katy, TX (US)

(73) Assignee: Best Medical International, Inc., Springfield, VA (US)

( * ) Notice: Subject to any disclaimer, the term of this patent is extended or adjusted under 35 U.S.C. 154(b) by 1576 days.

This patent is subject to a terminal disclaimer.

(21) Appl. No.: 11/005,643

(22) Filed: Dec. 6, 2004

(65) Prior Publication Data

US 2006/0122502 A1  Jun. 8, 2006

(51) Int. Cl.
*A61N 5/10* (2006.01)
(52) U.S. Cl. ....................................................... 378/65
(58) Field of Classification Search ................... 378/65, 378/62, 64, 162–166, 207
See application file for complete search history.

(56) References Cited

U.S. PATENT DOCUMENTS

| | | | |
|---|---|---|---|
| 3,861,807 A | 1/1975 | Lescrenier et al. |
| 3,987,281 A | 10/1976 | Hodes et al. |
| 4,455,609 A | 6/1984 | Inamura et al. |
| 5,373,844 A | 12/1994 | Smith et al. |
| 5,511,549 A | 4/1996 | Legg et al. |
| 5,596,619 A | 1/1997 | Carol |
| 5,754,623 A | 5/1998 | Seki et al. |
| 5,772,594 A | 6/1998 | Barrick |
| 6,032,066 A | 2/2000 | Lu et al. |
| 6,360,116 B1 | 3/2002 | Jackson et al. |
| 6,405,072 B1 | 6/2002 | Cosman |
| 6,435,717 B1 | 8/2002 | Kohler et al. |
| 6,535,574 B1 | 3/2003 | Collins et al. |
| 6,560,311 B1 | 5/2003 | Shepard et al. |
| 2002/0080915 A1 | 6/2002 | Frohlich |
| 2002/0122530 A1 | 9/2002 | Erbel et al. |
| 2002/0193685 A1 | 12/2002 | Mate et al. |
| 2004/0015077 A1 | 1/2004 | Sati et al. |
| 2004/0122311 A1 | 6/2004 | Cosman |
| 2004/0138556 A1 | 7/2004 | Cosman |
| 2005/0020917 A1 | 1/2005 | Scherch |

FOREIGN PATENT DOCUMENTS

| | | |
|---|---|---|
| DE | 103 35 037 A1 | 3/2005 |
| EP | 0 910 990 A1 | 4/1999 |
| EP | 0911065 A | 4/1999 |

(Continued)

*Primary Examiner*—Irakli Kiknadze

(57) ABSTRACT

A system to analyze the geometry of a radiation treatment apparatus, software, and methods are provided. The system includes an apparatus having a rotating assembly and a trackable body or plurality of trackable bodies, to mark a location of a preselected portion of the rotating assembly. The system also includes a trackable reference fixture and can include a constant orientation trackable body. A determiner determines the position and/or orientation of the trackable bodies, the trackable reference fixture, and constant orientation trackable body. The determiner then determines the geometry of the treatment apparatus to analyze a coordinate system used by an operator. The determiner can have a memory and geometry analyzing software stored in the memory to analyze the treatment apparatus geometry.

58 Claims, 10 Drawing Sheets

FOREIGN PATENT DOCUMENTS

| | | |
|---|---|---|
| EP | 1041918 | 11/2000 |
| EP | 1 419 801 A | 5/2004 |
| WO | WO 99/27839 A2 | 6/1999 |
| WO | WO 00/47103 A2 | 8/2000 |
| WO | WO 00/56215 A1 | 9/2000 |
| WO | WO 01/06924 A1 | 2/2001 |
| WO | WO 02/09588 A | 2/2002 |
| WO | WO 02/49044 A2 | 6/2002 |
| WO | WO 2005/018734 A | 3/2005 |
| WO | WO 2005/099819 A | 10/2005 |

SYSTEM FOR ANALYZING THE GEOMETRY OF A RADIATION TREATMENT APPARATUS, SOFTWARE AND RELATED METHODS

BACKGROUND OF THE INVENTION

1. Field of the Invention

The present invention relates to radiation therapy. More specifically, the present invention relates to a system, apparatus, software, and related methods for analyzing a geometry of a patient treatment apparatus.

2. Description of the Related Art

Radiation therapy can be effective in treating certain types of cancerous tumors, lesions, or other "targets." A vast majority of such targets can be eradicated completely if a sufficient radiation dose is delivered to the tumor or lesion volume. Complications, however, may result from use of the necessary effective radiation dose, due to damage to healthy tissue which surrounds the target, or to other healthy body organs located close to the target. The goal of various radiation procedures such as conformal radiation therapy treatment is to confine the delivered radiation dose to only the target volume defined by the outer surfaces of the target, while minimizing the dose of radiation to surrounding healthy tissue or adjacent healthy organs. If the effective radiation dose is not delivered to the proper location within the patient, serious complications may result.

Radiation therapy treatment typically uses a radiation delivery apparatus, such as, for example, a linear accelerator or other radiation producing source, to treat the target. The conventional linear accelerator includes a rotating gantry which generally rotates about a horizontal axis and which has a radiation beam source positionable about the patient which can direct a radiation beam toward the target to be treated. The linear accelerator can also include a rotating treatment table which generally rotates about a vertical axis and which can position the target within a rotational plane of the rotating gantry. Various types of devices or apparatus can further conform the shape of the radiation treatment beam during rotation of the radiation beam source to follow the spatial contour of the target, as viewed with respect to the radiation treatment beam, as it passes through the patient's body into the target. Multileaf collimators, for example, having multiple leaf or finger projections can be programmed to move individually in to and out of the path of the radiation beam to shape the radiation beam.

Various types of radiation treatment planning systems can create a radiation treatment plan which, when implemented, will deliver a specified dose of radiation shaped to conform to the target volume, while limiting the radiation dose delivered to sensitive surrounding healthy tissue or adjacent healthy organs or structures. Typically, the patient has the radiation therapy treatment plan prepared based upon a diagnostic study utilizing computerized tomographic ("CT") scanning, magnetic resonance ("MR") imaging, or conventional simulation films which are plain x-rays generated with the patient. This radiation therapy treatment plan is developed such that the patient's tumor or lesion is in the position that will be used during the radiation therapy treatment.

Regardless of which technique is used at the time of the diagnostic study to develop the radiation therapy treatment plan, in the delivery of either conformal radiation therapy treatments or static radiation therapy treatments, the position of the target with respect to the radiation delivery device or apparatus is very important. Successful radiation therapy depends on accurately placing the radiation beam in the proper position upon the target. Thus, it is necessary to relate the position of the target at the time of the diagnostic study to how the target will be positioned at the time of the radiation therapy treatment. It is also necessary to maintain an alignment between the radiation delivery device or apparatus and the target throughout the delivery of the radiation therapy. If this positional relationship is not correct, the radiation dose may not be delivered to the correct location within the patient's body, possibly under-treating the target tumor or lesion, and damaging healthy surrounding tissue and organs.

Thus, proper radiation therapy depends on accurately placing radiation beams in a proper juxtaposition with the patient to be treated. This can be accomplished by referencing both the radiation beam and the patient position to a coordinate system referred to as the isocenter coordinate system, which is defined by the geometry of the radiation delivery device or apparatus. In the linear accelerator example, the gantry, the treatment table, and collimator each have axes of rotation designed to intersect at a specific position in the middle of a treatment room, referred to as the isocenter, the origin of the isocenter coordinate system. The isocenter coordinate system is typically nominally defined as horizontal x-axis), vertical (z-axis), and co-linear with the axis of gantry rotation (y-axis). The intersection (isocenter) of these three axis of interest is determined and used as a reference "point" to orient the target to the radiation treatment plan and for execution subsequent radiation delivery.

In order to deliver the radiation therapy in accordance with the radiation plan, the position of the patient is generally adjusted to dispose the target at the isocenter of the linear accelerator. That is, the patient is positioned on the treatment table of the radiation delivery device or apparatus to conform to the position used during formulation of the treatment plan. The treatment table is rotated to dispose the target at the isocenter to align the view of the target with that view expected by the collimator or other radiation delivery device of the linear accelerator, according to the radiation treatment plan. The treatment table is then locked in place, and the patient is immobilized so that the radiation therapy treatment can be started.

In the linear accelerator example, the isocenter can be considered to be the point where the radiation beams from the collimator intersect as the gantry of the linear accelerator carrying the radiation beam source rotates around the target in the patient. There are various methodologies of determining the location of this isocenter. For example, one methodology of determining the isocenter includes attaching a marking device to the gantry, such as a long rod holding a marking implement, and positioning a vertically oriented sheet of receiving material, such as paper, adjacent the marking device. The gantry is then rotated to form an arc or a circle on the receiving material. The operator can then examine the arc or circle to determine the origin of the arc or circle, which relates to the isocenter. Also, for example, the operator can actually deploy the radiation beam in order to measure the direction of the radiation beam during rotation of the gantry, to thereby determine the location of the isocenter. Other physical measurements can also be taken to help the operator determine an approximate location of the isocenter. Lasers, typically mounted on the wall of the treatment room, are pointed or directed to cross at this isocenter to identify the predetermined location of the isocenter. Phantoms (patient structure simulators) positioned on the treatment table are typically utilized to perform such laser alignment.

Recognized by the Applicant, however, is that current methods of determining the isocenter are difficult and time-consuming and have inherent inaccuracies because they, at least in the linear accelerator example, fail to properly account for the collimator and/or the treatment table. Also, the mechanical systems including the gantry, collimator, and treatment table are known to be imperfect, and thus, do not produce absolutely true circular arcs of rotation. For example, the bearings of the linear accelerator are not true spheres and the gantry itself may tend to sag. Thus, the arc or circle formed to determine the location of the isocenter are imperfect, and therefore, do not produce perfect centers of rotation nor perfect axes of rotation. This results in a non-precise isocenter position. The state-of-the-art tends to ignore or misinterpret these imperfections, and therefore, produces an inherently inaccurate isocenter position.

Also, as described above, recognized is that lasers are known to drift and in other ways degrade in performance. Thus, the lasers can result in further inaccuracies being inherently added to the isocenter position which need be precise to properly define the coordinate system used by the operator to deliver the correct radiation treatment. Recognized, therefore, is the need for a system, software, and methods that can precisely measure the rotation of various components of the mechanical system of the radiation treatment device or apparatus to determine the location of the radiation beam (e.g. from the geometry of the gantry and collimator) and the positioning of the patient (e.g. from the geometry of the treatment table) in order to precisely define the coordinate system used by the operator to deliver the correct treatment.

SUMMARY OF THE INVENTION

In view of the foregoing, embodiments of the present invention advantageously provide a system, software, and methods related to measuring and capturing the geometry of a radiation treatment apparatus to determine the origin and directions of a coordinates system used during radiation treatment. Advantageously, embodiments of the present invention include a system, software, and methods that can precisely measure the rotation of various rotating assemblies of the mechanical system of the radiation treatment apparatus. This information can be used to determine the location of the radiation beam and the positioning of the patient in order to precisely define the isocenter coordinate system used by the operator to deliver the correct treatment. Advantageously, embodiments of the present invention also provide a system including a trackable body, software, and process that can measure three-dimensional points in space at locations along the maximum rotational arc or path of rotating assemblies of a radiation treatment device or apparatus such as a gantry, collimator, and treatment table of a linear accelerator. These measurements can be used to adapt the planned radiation treatment to improve its accuracy and efficiency. Advantageously, errors and imperfections in the mechanical system of the radiation treatment device or apparatus that might normally be ignored or misinterpreted can be analyzed and indicated.

Embodiments of the present invention provide a system to analyze a geometry of a radiation treatment apparatus to determine a location of an origin and an orientation of a coordinate system used to reference radiation beam and patient positioning so that a treatment plan can be more accurately applied to the patient. In the preferred embodiment of the present invention, the system generally includes a treatment apparatus, typically in the form of a linear accelerator, having a plurality of a rotating assemblies controlled by a controller which receives instructions from an application computer. The system includes a trackable body or plurality of trackable bodies having indicators connected thereto. Each trackable body is positioned to mark a location of a preselected portion of a rotating assembly of the treatment apparatus. The system can also include a trackable reference fixture and a constant orientation trackable body adapted to be connected to one of the rotating assemblies, each also having indicators connected thereto. A detector is provided to detect the position of the indicators. A determiner, in communication with a detector, determines the position and/or orientation of the trackable body or bodies, the trackable reference fixture, and constant orientation trackable body, to thereby determine the geometry of the treatment apparatus, and to thereby analyze the coordinate system used by a therapist (referred to as the isocenter coordinate system). An array of lasers can be used in conjunction with a trackable laser alignment body to mark a determined origin of the isocenter coordinate system referred to as the isocenter.

More specifically, in the preferred embodiment of the present invention, the system includes a radiation treatment apparatus which delivers radiation to a target in a patient. The radiation treatment apparatus includes a plurality of rotating assemblies, each functioning to direct a radiation beam through a target of a patient and each having a rotational path in a distinct plane and an axis of rotation. The axis of rotation of each rotating assembly generally intersects the axis of rotation of each other rotating assemblies at a substantially same three-dimensional coordinate which defines the isocenter or origin of the isocenter coordinate system of the treatment apparatus. A plurality of preferably optically trackable bodies, each having a plurality of indicators preferably in the form of optical retro-reflective spheres mounted thereto, can be connected to a preselected portion of a respective one of the plurality of rotating assemblies of the treatment apparatus. The trackable bodies can provide the system the ability to sample three-dimensional coordinate positions of the preselected portion of each rotating assembly along a rotational path. A preferably optical detector or camera subsystem has a detector body positioned spaced apart from the trackable bodies at a preselected three-dimensional detector reference location and at least one but preferably a pair of optical receivers connected to the detector body. Each of the optical receivers is positioned to receive energy from each of the plurality of indicators of the trackable bodies in view of the receivers to detect a three-dimensional position of the plurality of indicators so that during rotation of the plurality of rotating assemblies the detector produces a plurality of position signals indicating three-dimensional coordinate positions located along the rotational path of the preselected portion of each respective one of the plurality of rotating assemblies.

Note, the function of the plurality of trackable bodies can be achieved through use of a single trackable body sequentially connected to the preselected portion of one of the plurality of rotating assemblies, separately rotated with the respective rotating assembly prior to connecting the trackable body to another one of the plurality of rotating assemblies, and viewed by the detector prior to connecting the optically trackable body to another one of the plurality of rotating assemblies.

A determiner, in communication with the detector, and responsive to the plurality of position signals produced by the detector during rotation of the one of the plurality of rotating assemblies, determines the set of three-dimensional coordinate positions for the preselected portion of each one of the plurality of rotating assemblies and determines the axis of rotation for each one of the plurality of rotating assemblies. The axis of rotation of each of the assemblies can be used to determine the isocenter of the radiation treatment apparatus. The function of the determiner can be implemented in hardware and/or software, however, in the preferred embodiment of the present invention, the determiner is implemented almost entirely in software. Correspondingly, the determiner can be in the form of a relatively simple computer having a memory and geometry analyzing software stored in the memory to analyze radiation treatment apparatus geometry, to thereby determine the isocenter of the radiation.

The system also includes a trackable reference fixture connected to a preselected portion of preferably the most visible rotating assembly which can provide a ready reference to the determined three-dimensional coordinate position of the isocenter. The system can also include a constant orientation trackable body, which can be part of the trackable reference fixture or separately connected to a preselected portion of the rotating assembly carrying the trackable reference fixture. The constant orientation trackable body can further provide a reference orientation used by the determiner to determine an angle of rotation of the rotating assembly, which allows the determiner to determine an angular difference between a preselected orientation of the isocenter coordinate system and an orientation of the isocenter coordinate system determined with respect to the trackable reference fixture when the rotating assembly is rotated from its initial reference position. Thus, the determiner can readily determine the position and orientation of the trackable reference fixture and constant orientation trackable body, with respect to the detector. Advantageously, an accurate reference position and orientation of the isocenter can be easily provided regardless of any changes in the rotational orientation of the trackable reference fixture resulting from rotation of the rotating assembly.

Embodiments of the present invention are not limited to use on radiation treatment apparatus but can be used on any apparatus having rotating assemblies which intersect at a point or area of interest. For example, in an embodiment of the present invention, a system to analyze a geometry of an apparatus includes an apparatus that includes a plurality of rotating assemblies each having a rotational path in a distinct plane and an axis of rotation. The axis of rotation of each rotating assembly intersects the axis of rotation of each other rotating assembly of the plurality of rotating assemblies at a substantially same three-dimensional coordinate defining an isocenter of the apparatus. A trackable body is connected to a preselected portion of one of the plurality of rotating assemblies of the apparatus and has a plurality of indicators mounted thereto. A detector having a detector body positioned spaced apart from the trackable body and a receiver positioned to receive energy from the plurality of indicators of the trackable body detects a three-dimensional indicator position of the plurality of indicators so that during rotation of the one of the plurality of rotating assemblies the detector produces a plurality of position signals indicating the three-dimensional indicator position of the plurality of indicators. A determiner, in communication with the detector and responsive to the plurality of position signals produced by the detector during rotation of the one of the plurality of rotating assemblies, determines a set of three-dimensional coordinate positions for the preselected portion of the one of the plurality of rotating assemblies located substantially along the rotational path of the preselected portion of one of the plurality of rotating assemblies. From this, the determiner can determine the axis of rotation for the one of the plurality of rotating assemblies. Utilizing the same methodology, the determiner can determine a separate set of three-dimensional coordinate positions of the preselected portion for each of at least two of the plurality of rotating assemblies, to thereby determine the axis of rotation for the at least two of the plurality of rotating assemblies and an intersection of the axis of rotation of the at least two of the plurality of rotating assemblies. This intersection substantially indicates the three-dimensional coordinate position of the isocenter of the apparatus.

As stated above, embodiments of the present invention include geometry analyzing software to analyze the geometry of an apparatus having a plurality of rotating assemblies, such as, for example, the geometry for the above described apparatus and radiation treatment apparatus. In an embodiment of the present invention, the geometry analyzing software includes a position determiner, which receives and is responsive to a plurality of position signals from the detector, to determine or form at least two but preferably three sets of three-dimensional coordinate positions, each set representing three-dimensional coordinate sampled data points or positions located substantially along the maximum rotational arc or path of the preselected portion of a respective one of the rotating assemblies. With appropriate filtering and smoothing, an arc determiner, responsive to the position determiner, determines a fit of a separate arc for each set of three-dimensional coordinate sampled data points or positions of the respective rotating assembly. Each fitted arc indicates the rotational path of the preselected portion of a respective one of the rotating assemblies and is normally positioned in a plane substantially orthogonal to that of each other fitted arc. An axis determiner, responsive to the arc determiner, determines a center of rotation and a normal for each fitted arc indicating the axis of rotation of the respective rotating assembly. Further, an intersection determiner, responsive to the axis determiner, determines an intersection of the axis of rotation for at least two of the rotating assemblies, the intersection substantially indicating the three-dimensional coordinate position of the isocenter of the isocenter coordinate system.

When the trackable fixture is fixedly connected to a rotating assembly, it can provide a reference to the determined three-dimensional coordinate position of the isocenter. That is, the geometry analyzing software can include a transform determiner which can utilize the determined three-dimensional coordinate position of the isocenter to determine a transform matrix between the determined three-dimensional coordinate position of the isocenter of the radiation treatment apparatus and the trackable fixture. This allows the detector to be moved without losing a readily determined reference to the three-dimensional coordinate position of the isocenter. The trackable fixture, being connected to a rotating assembly, however, by its nature has a variable orientation with respect to the orientation of the axis of the isocenter coordinate system. In an embodiment of the present invention, the software includes a position determiner that can receive a first plurality of position signals to determine a position and an orientation of the trackable fixture. A constant orientation trackable body, having an orientation that remains constant during rotation of the rotating assembly, can be connected to the rotating assembly to compensate for an error in the determined orientation of the axis of the isocenter coordinate system caused by rotation of the trackable fixture from an initial reference position. Thus, the position determiner can further receive a second plurality of position signals to determine a position and an orientation of a constant orientation trackable body. A rotation angle determiner, responsive to the position determiner, can determine an angular difference between the orientation of the variable orientation trackable fixture and the orientation of the constant orientation trackable body. This angular difference indicates an angle of rotation of the variable orientation trackable reference fixture, and thus, an angle of rotation of the rotating assembly. The angle of rotation can be used to formulate a correction factor so that an isocenter position determiner can determine the position and the orientation of the isocenter with respect to the detector or with respect to the treatment apparatus or treatment room.

The software can also provide for extensive analysis of the geometry of the treatment apparatus. That is, the software can also include an imperfection identifier and an imperfection analyzer to respectively identify and analyze an effect from imperfections in the rotating assembly or assemblies on the determined three-dimensional position of the isocenter, when so existing.

Also for example, in an embodiment of the present invention, the system includes geometry analyzing software that can include a position determiner that can receive a first plurality of position signals, to determine a position and an orientation of a variable orientation trackable reference fixture connected to a rotating assembly of an apparatus. The variable orientation trackable reference fixture has an orientation that varies during rotation of the rotating assembly. The position determiner can also receive a second plurality of position signals, to determine a position and an orientation of a constant orientation trackable body connected to the rotating assembly of the apparatus. The constant orientation trackable body has an orientation that remains constant during rotation of the rotating assembly. A rotation angle determiner, responsive to the position determiner, determines an angular difference between the orientation of the variable orientation trackable fixture and the orientation of the constant orientation trackable body. The angular difference indicates an angle of rotation of the variable orientation trackable reference fixture and an angle of rotation of the rotating assembly. A predetermined transform matrix that indicates a magnitude, direction, and/or a coordinate system rotation between the variable orientation trackable reference fixture and a predetermined isocenter of the apparatus can be stored on the storage media. An isocenter position determiner, responsive to the position determiner and positioned to receive the predetermined transform matrix from the storage media, can determine a relative position of the isocenter from the variable orientation trackable reference fixture. An isocenter coordinate system orientation determiner, responsive to the rotation angle determiner and isocenter position determiner, can determine an orientation of the isocenter coordinate system.

Embodiments of the present invention also include a computer readable medium that is readable by a computer to analyze the geometry of an apparatus having a plurality of rotating assemblies. For example, in an embodiment of the present invention the computer readable medium comprises a set of instructions that, when executed by the computer, cause the computer to perform the operations of receiving a plurality of position signals, determining at least two sets of three-dimensional coordinate positions substantially located along a separate rotational path of a preselected portion of a respective at least two rotating assemblies of the apparatus, and responsive to the plurality of position signals, determining a fit of a separate arc to each of the at least two sets of three-dimensional coordinate positions. Each fitted arc indicates the rotational path of the preselected portion of one of the at least two rotating assemblies and is positioned in a plane substantially orthogonal to that of each other fitted arc. The instructions also include those for determining a center of rotation and a normal for each fitted arc indicating the respective axes of rotation of each of the at least two rotating assemblies, and determining an intersection of the axes of rotation of the at least two rotating assemblies. The intersection substantially indicates a three-dimensional coordinate position of an isocenter of an isocenter coordinate system.

Also for example, in an embodiment of the present invention, the computer readable medium comprises a set of instructions that, when executed by the computer, cause the computer to perform the operations of receiving a first plurality of position signals, and determining a position and an orientation of a variable orientation trackable reference fixture connected to a rotating assembly of the apparatus and having an orientation that varies during rotation of the rotating assembly. The instructions also include those for receiving a second plurality of position signals and determining a position and an orientation of a constant orientation trackable body connected to the rotating assembly of the apparatus and having an orientation that remains constant during rotation of the rotating assembly. The instructions further include those for determining an angular difference between the orientation of the variable orientation trackable fixture and the orientation of the constant orientation trackable body, the angular difference indicating an angle of rotation of the variable orientation trackable reference fixture and an angle of rotation of the rotating assembly.

The instructions can also include those for performing the operations of retrieving a predetermined transform matrix stored on the computer readable media, the predetermined transform matrix indicating a magnitude, direction, and/or a rotation between the variable orientation trackable reference fixture and a predetermined isocenter of the apparatus, and determining a relative position of the isocenter from the variable orientation trackable reference fixture, responsive to the determined position of the variable orientation trackable body and the predetermined transform matrix. The instructions can also include those for performing the operation of determining an orientation of the isocenter coordinate system, responsive to orientation of the variable orientation trackable fixture and the determined angular difference. This is accomplished by determining an angular difference between the orientation of the variable orientation trackable body and the orientation of the constant orientation trackable body.

Embodiments of the present invention also include methods for analyzing a geometry of an apparatus including a plurality of rotating assemblies, whereby each respective rotating assembly can have a preferably optically trackable body connected either sequentially or simultaneously to the rotating assembly at a preselected portion of each rotating assembly. For example, in an embodiment of the present invention, a trackable body is sequentially connected to at least two but preferably three rotating assemblies of the treatment apparatus. In another embodiment of the present invention, each of a plurality of trackable bodies are individually and separately connected to a respective one of the rotating assemblies for simultaneous viewing. Regardless of the embodiment selected, each of the plurality of rotating assemblies having a trackable body connected thereto can be rotated by the user and viewed. A detector detects the position of a subset of a plurality of indicators mounted to each trackable body during rotation and produces a plurality of position signals indicative of the position of each of a plurality of indicators when in view of the detector. The plurality of position signals provide data which can be used by a determiner to determine at least two sets of sampled three-dimensional coordinate points or positions in space substantially along a rotational path of the each rotating assembly being rotated with a trackable body and viewed with the detector. The determiner can categorize or form the sampled data points or positions into sets of three-dimensional coordinate points or positions, a separate set or sets for each rotating assembly being analyzed. With use of appropriate filtering and smoothing, a fit of a separate arc (a true arc or a circle) to each respective set of the sampled three-dimensional coordinate points or positions for each corresponding rotating assembly. Each fitted arc indicates the rotational path of the preselected portion of a respective one of the at least two rotating assemblies. Each fitted arc has a normal extending from a center of rotation of the arc which defines an axis of rotation for each respective rotating assembly. The three-dimensional coordinate position of the isocenter of an isocenter coordinate system can be readily determined by determining the intersection of at least two but, for an apparatus, such as a linear accelerator, preferably all three of the axes of rotation of the respective rotating assemblies associated with the respective arcs.

Once the three-dimensional coordinate position of the isocenter is determined, if not already installed, a trackable reference fixture can be connected or attached to a preselected portion of preferably the most visible rotating assembly to provide for calibration of the three-dimensional coordinate position of the trackable reference fixture to the determined three-dimensional coordinate position of the isocenter. This can be accomplished by determining a transform matrix between the predetermined trackable reference fixture three-dimensional coordinate position and the predetermined three-dimensional coordinate position of the isocenter. This transform matrix allows the trackable reference fixture to provide a relative reference to the three-dimensional coordinate position of the isocenter by determining a three-dimensional coordinate position of the trackable fixture at one of a plurality of three-dimensional coordinate positions located substantially along a rotational path of the rotating assembly and applying the transform matrix to the determined three-dimensional coordinate position of the trackable fixture. Advantageously, having this trackable reference fixture positioned close to the determined isocenter advantageously improves accuracy of the detector/determiner subsystem.

Also, for example, in an embodiment of the present invention, imperfections of the geometry of the treatment apparatus can also be determined. Each fitted arc can be considered to have its own dataset. That is, each respective fitted arc is comprised of data points (three-dimensional coordinate positions) forming a respective dataset of the three-dimensional coordinate data points or positions that fall along a curve defining the respective fitted arc. A comparison can be made between at least one, but preferably all, of the three-dimensional coordinate positions in one or more of the respective sets of the sampled three-dimensional coordinate positions to the three-dimensional coordinate positions in the dataset defining the respective fitted arc. Those points not considered to be substantially coincident, i.e., those that would not fall on the curve defining the respective fitted arc, indicate a relative position of an imperfection in the respective rotating assembly. An analysis can be made on an effect of the determined imperfections on the determined three-dimensional position of the isocenter and on and orientation of the isocenter coordinate system. Advantageously, knowledge of the effects of such imperfections allow a therapist to adapt, as necessary, a treatment plan which utilizes the determined isocenter.

Embodiments of the present invention also include methods for analyzing a geometry of an apparatus having a rotating assembly where a first transform matrix between a trackable reference fixture and a determined three-dimensional coordinate position of the isocenter has already been predetermined. For example, in an embodiment of the present invention, a method includes connecting a trackable reference fixture to a rotating assembly at a reference three-dimensional coordinate position relative to the isocenter of the treatment apparatus such that its orientation varies with the rotation of the rotating assembly. A camera subsystem or suitable trackable body detector subsystem is then positioned or optionally repositioned in a nonobstructive location. With the detector viewing the trackable reference fixture, the detector can detect the trackable reference fixture and a computer (e.g. determiner) can determine a second transform matrix between the three-dimensional coordinate position of the trackable body and the three-dimensional coordinate position of the trackable reference fixture. The determiner can also receive the predetermined first transform matrix to thereby transform the three-dimensional coordinate position of the isocenter to detector/camera space. The trackable reference fixture, being connected to a rotating assembly, however, by its nature, can generally only provide a three-dimensional coordinate position of the isocenter having coordinate system axes oriented relative to the orientation of the trackable reference fixture, which is variable.

To determine or to correct the orientation of the isocenter coordinate system, a constant orientation trackable body can be pivotally connected on one end to either the trackable reference fixture or separately connected to a preselected portion of the rotating assembly. A pendulum-type action of the constant orientation trackable body provides a reference orientation which allows the determiner to correct the orientation of isocenter determined with reference to the trackable reference fixture. This orientation discrepancy results from a rotational error which can exist when the rotating assembly carrying the trackable reference fixture is rotated off its initial reference position. That is, advantageously, the user can rotate the rotating assembly and still obtain an accurate orientation of the isocenter coordinate system. The determiner first determines the orientations of the trackable reference fixture and the constant orientation trackable body. The determiner can then determine the rotation angle of the trackable reference fixture, which relates to the rotational position of the rotating assembly from an initial reference position. This can be accomplished by determining an angular difference between the trackable reference fixture and the constant orientation trackable body. The position and true or selected orientation of the isocenter can be determined by conceptually rotating the reference orientation of the isocenter, determined from the trackable reference fixture, by an amount related to the angular difference between the trackable reference fixture and the constant orientation trackable body. Thus, advantageously, an accurate reference position and orientation of the isocenter is provided regardless of the rotational orientation of the trackable reference fixture, which can vary due to rotation of the rotating assembly for which the trackable reference fixture is connected.

Advantageously, embodiments of the present invention negate the requirement for arduous manual steps to determine the isocenter of an apparatus, such as, for example, a linear accelerator. The embodiments of the present invention can measure and determine the isocenter using a very accurate tracking system, reducing the reliance on laser and manual systems with known drift and inaccuracy characteristics. Advantageously, embodiments of the present invention provide the ability to align isocenter display lasers to the actual mechanical system of the treatment apparatus, provide the ability to determine the existence of laser drift, and with modifications and additions, can provide continuous verification of the accuracy of the system during treatment. Advantageously, embodiments of the present invention can include an optical tracking device which can incorporate a mechanical quick disconnect to allow ready attachment to and removal from various rotating assemblies of the radiation treatment apparatus.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Successful therapy treatments, such as, for example, radiation therapy, rely on the ability to accurately locate and define a radiation beam. The spatial position of the radiation beam is defined by the physical geometry of the radiation treatment apparatus. Embodiments of the present invention analyze the geometry of rotating assemblies of the radiation treatment apparatus to define a coordinate system of the radiation treatment apparatus, which is used by a therapist to determine the position of the radiation beam and the positioning of the patient. As illustrated in FIGS. 1-11, embodiments of the present invention provide a system, software, and methods for analyzing such geometry of an apparatus to determine the origin and orientation of the coordinate system used. This origin is referred to as "isocenter" and this coordinate system is referred to as the "isocenter coordinate system."

Figure 1:
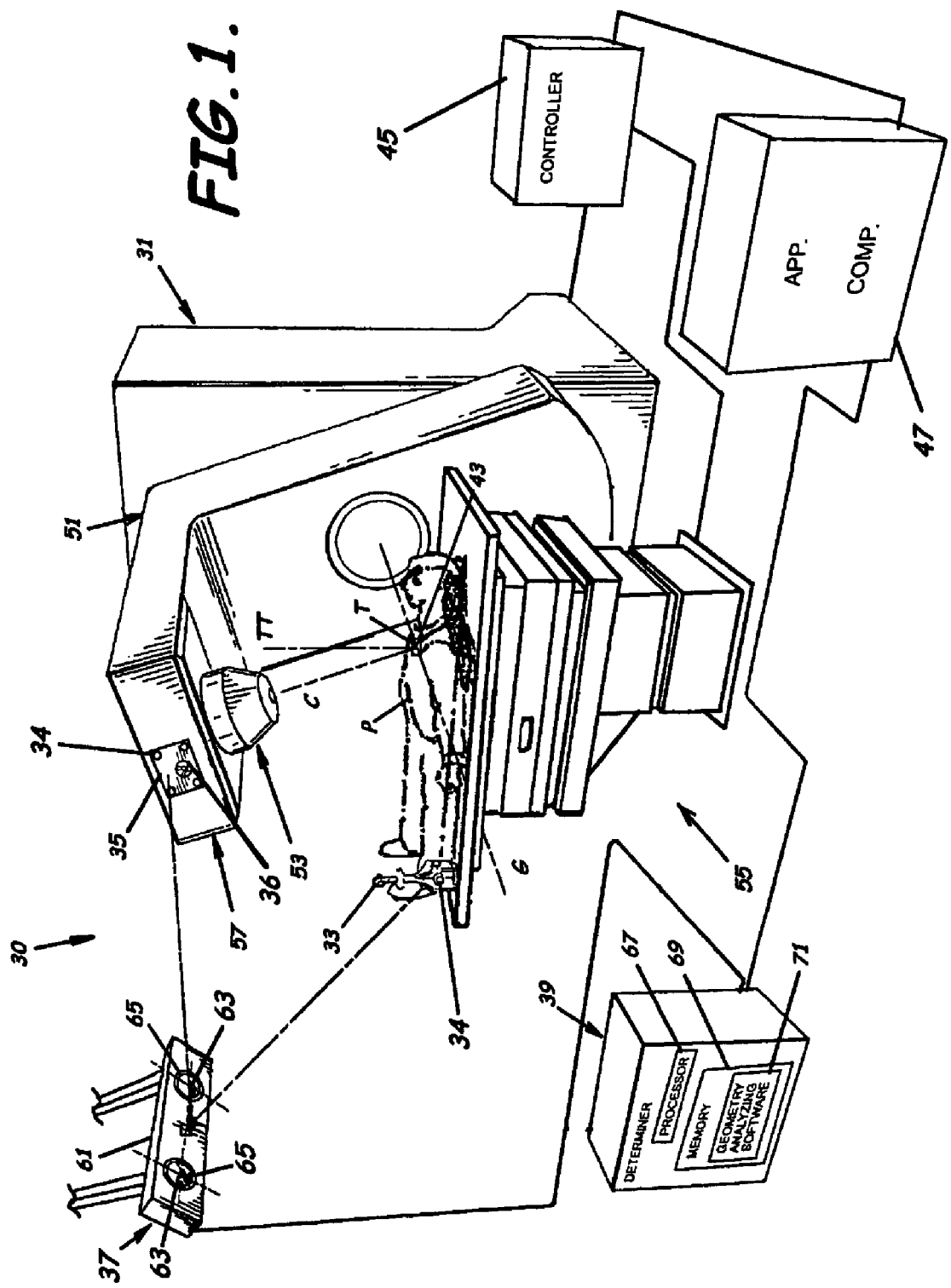
FIG. 1 is a perspective view of a system to analyze a geometry of a radiation treatment apparatus according to an embodiment of the present invention.

As perhaps best shown in FIG. 1, the system 30 generally includes an apparatus, typically in the form of a linear accelerator 31, a trackable body or bodies 33, each including a plurality of indicators 34 and positioned to mark a location of a preselected portion of a rotating assembly of the treatment apparatus, a trackable reference fixture 35, and optionally a constant orientation trackable body 36. The system 30 also includes a detector 37 to detect the position of the plurality of indicators 34 used to determine the position and/or orientation of the trackable body 33, the trackable reference fixture 35, and constant orientation trackable body 36, and a determiner 39 to determine the geometry of the treatment apparatus and to analyze the isocenter coordinate system of the treatment apparatus used by a therapist. The system 30 can also include an array of lasers 41 (FIG. 6) used in conjunction with a trackable laser alignment body 42 to visibly mark the origin of the isocenter coordinate system referred to as the isocenter 43. When the apparatus is in the form of a treatment machine, the system 30 also includes an apparatus controller 45 and an application computer 47, which provides the apparatus controller 47 instructions to deliver a treatment plan.

More specifically, the system 30 includes a treatment apparatus, illustrated as a linear accelerator 31, which delivers radiation to a target T in a patient P. The linear accelerator 31 has a plurality of rotating assemblies including a rotating gantry assembly 51, a rotating beam collimator assembly 53, and a rotating treatment patient table assembly 55. Each rotating assembly functions to direct a radiation beam through a target T of a patient P. Each rotating assembly has a rotational path in a distinct plane and an axis of rotation. The rotating gantry assembly 51 has a gantry axis of rotation G and a gantry head 57 positioned adjacent the gantry rotational outer circumference to direct a radiation beam toward the gantry axis of rotation G. The rotating beam collimator assembly 53 is connected to the gantry head 57. The rotating beam collimator assembly 53 has a collimator axis of rotation C positioned coaxially with a central axis of the radiation beam directed by the gantry head 57 to shape the profile of the radiation beam. The rotating patient treatment table assembly 55 has a treatment table axis of rotation TT and is positioned adjacent the gantry assembly 51 to move the position of the target T of the patient P with respect to the isocenter 43 before and during treatment. The axis of rotation G, C, TT, of each rotating assembly 51, 53, 55, generally intersect the axis of rotation of each other rotating assembly at a substantially same three-dimensional coordinate which defines the isocenter 43 of the linear accelerator 31.

A trackable body 33 having a plurality of indicators 34 mounted thereto, such as, for example, that disclosed in U.S. patent application Ser. No. 10/957,128 by Smetak et al., titled "System and Tracker for Tracking an Object, and Related Methods" or a suitable substitute, can be sequentially connected to a preselected portion of each rotating assembly 51, 53, 55, to provide rotational path data for each of the rotating assemblies 51, 53, 55, when so connected. The trackable body 33 can be used to determine the axis of rotation G, C, TT, for each of the rotating assemblies 51, 53, 55. Alternatively, each rotating assembly 51, 53, 55, can simultaneously have a separate trackable body 33 individually connected (see FIG. 3). In the preferred embodiment of the present invention, the indicators 34 of the trackable body 33 are passive indicators in the form of optical retro-reflective spheres. Passive indicators provide an additional advantage in that they do not require wiring or fiber optics. This allows the trackable body 33 to be easily connected and disconnected from a predetermined portion of either or all of the rotating assemblies 51, 53, 55.

Figure 3:
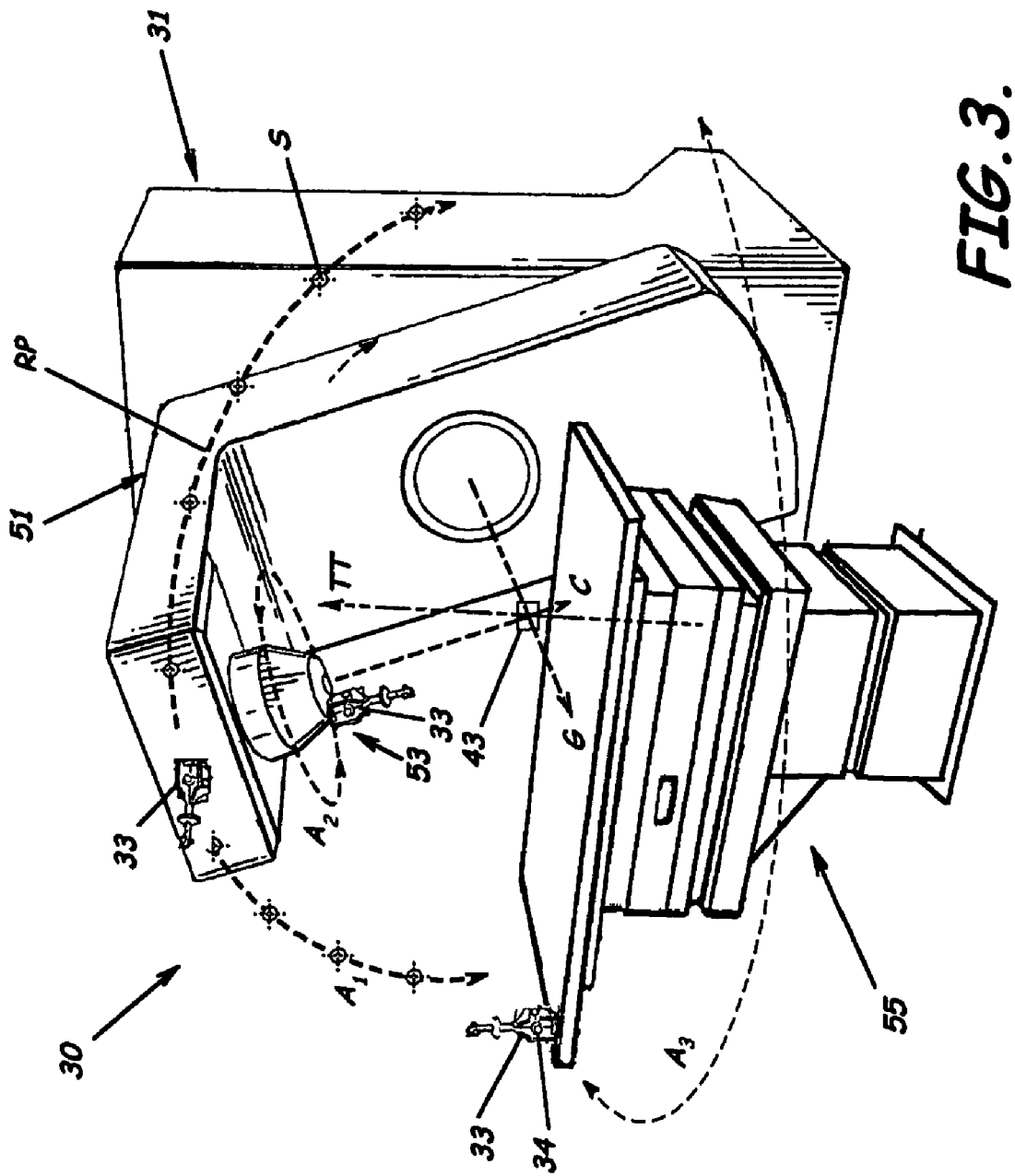
FIG. 3 is a perspective view of a treatment apparatus illustrating sampled data positions along a rotational path of a rotating assembly according to an embodiment of the present invention.
Figure 4:
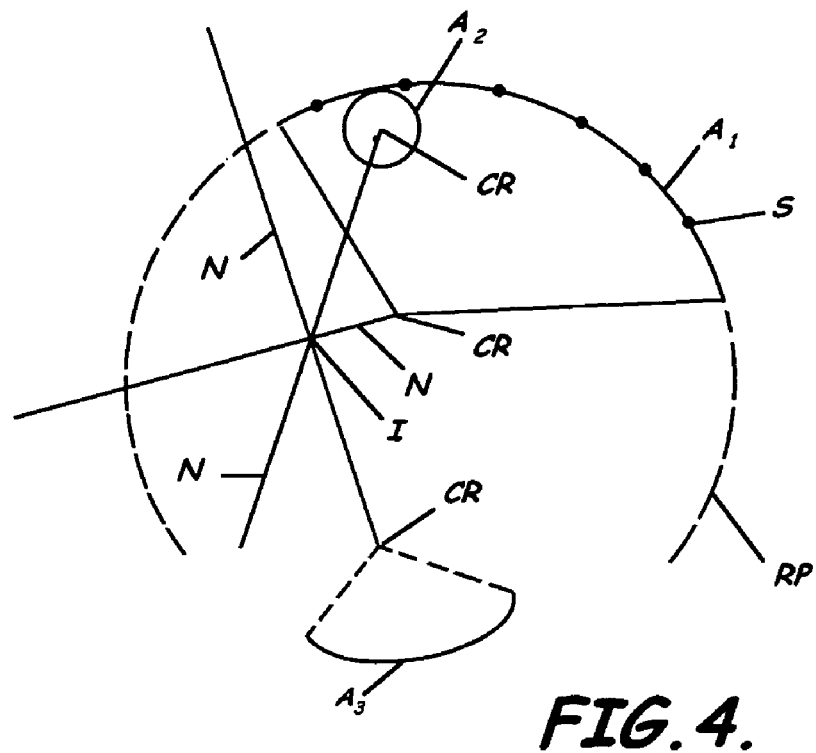
FIG. 4 is a graphical depiction of a trio of arcs fitted to the treatment apparatus of FIG. 3 and having intersecting axes according to an embodiment of the present invention.

The system 30 includes a detector 37 having a detector body 61 positioned spaced apart from the trackable body or bodies 33 and at least one but preferably a plurality of receivers 63 positioned to receive energy from the plurality of indicators 34 of the trackable body 33. The detector 37 can detect a three-dimensional indicator position of the indicators 34 which translate to a position and/or orientation of the trackable body or bodies 33. As illustrated in FIG. 3 for rotating assembly 51, when a trackable body 33 is connected to a preselected portion of either the rotating assemblies 51, 53, 55, located other than at the axis of rotation, and is rotated with the respective rotating assembly 51, 53, 55, the detected positions of the indicators 34 of the trackable body 33 further translate to a set of three-dimensional coordinate sampled data points or positions for the respective rotating assembly 51, 53, 55, such as the illustrated positions S for rotating assembly 51. That is, for each of the rotating assemblies 51, 53, 55, having a trackable body 33 connected thereto, during rotation of the respective rotating assembly or assemblies 51, 53, 55, the detector 37 produces a plurality of position signals indicating the positions of the indicators 34 of each trackable body 33 in view of the detector 37. From the position signals, a determiner 39 (described later) can determine a set of three-dimensional coordinate sampled data points or positions located along the rotational path of the preselected portion of the respective rotating assembly 51, 53, or 55, such as the illustrated positions S located along rotational path RP for rotating assembly 51.

As stated above, the trackable body 33 can be implemented using preferably passive indicators 34 such as retro-reflective spheres. Correspondingly, the detector 37 is preferably an optical detector or camera locator subsystem, such as, for example, a camera or opti-electrical motion measurement system, known as the Polaris®, by Northern Digital Inc., Ontario Canada, having a pair of optical receivers 63, each with a field of view and adapted to receive optical energy emitted or reflected by each of the plurality of indicators 34 when positioned in the field of view. In this form, the receivers 63 can detect the three-dimensional sphere position of each of the plurality of indicators 34 of the trackable body 33 when positioned simultaneously within the field of view of both of the optical receivers 63 to produce the plurality of position signals. When the plurality of indicators 34 are in the form of optical retro-reflective spheres, the detector 37 can include a pair of infrared illuminators 65, each separately positioned adjacent one of the receivers 63, to selectively illuminate each of the plurality of indicators 34 when positioned in the field of view of the respective adjacent receiver 63.

The system 30 also includes a determiner 39 having a processor 67 and memory 69 and which communicates with the detector 37 to receive and process the plurality of position signals produced by the detector 37 during rotation of the rotating assembly or assemblies 51, 53, 55. The determiner 39 determines the respective set or sets of three-dimensional coordinate sampled positions for the preselected portion of the respective rotating assembly or assemblies 51, 53, 55, such as the illustrated positions S located along rotational path RP for rotating assembly 51. These respective sets of sampled positions are than utilized to thereby determine the respective axis of rotation G, C, TT, for the respective rotating assembly or assemblies 51, 53, 55. In the illustrated embodiment (FIG. 3), the determiner 39 can determine the isocenter 43 by determining an intersection of at least two but preferably all three of the respective axes of rotation G, C, TT. The function of the determiner 39 can be implemented in hardware and/or software, however, in the preferred embodiment of the present invention, determiner 39 is implemented almost entirely in software. Correspondingly, memory 69 of the determiner 39 can include geometry analyzing software 71 to analyze the geometry of the rotating assemblies 51, 53, 55, of the radiation treatment apparatus (linear accelerator 31).

Note, although described as positioned within memory 69 of the determiner 39, all or a portion of the geometry analyzing software 71 can be located in both the detector 37 and the determiner 39, and/or partially or solely in a remote computer (not shown). In fact, although illustrated and described for simplicity as being solely located in the determiner 39, in the preferred embodiment of the invention, the software 71 is at least partially located in the detector 37. Thus, the physical embodiment of the detector 37 also can include a portion of the physical and the functional embodiment of the determiner 39. To this end, the detector 37 typically includes its own processor and memory (not shown). Nevertheless, regardless of the physical or functional positioning, the determiner 39 advantageously determines the three-dimensional coordinate position of the isocenter 43 from the mechanical systems (rotating assembly or assemblies) of the treatment apparatus, which is then used as a reference point for patient analysis, treatment planning, and/or for treatment delivery.

The system 30 can also include a trackable reference fixture 35 preferably connected to a preselected portion of the most visible rotating assembly, which, in the linear accelerator example, is the gantry head 57 of the rotating gantry assembly 51. When properly calibrated to the detector 37, the trackable reference fixture 35 provides a ready reference to the determined three-dimensional coordinate position and assigned orientation of the isocenter 43. The determiner 39 can determine a transform matrix M, illustrated as an arrow (FIG. 5), between the trackable reference fixture 35 and the isocenter 43, which will allow the determiner 39 to determine or reacquire the relative three-dimensional coordinate position and orientation of the isocenter 43 even after the three-dimensional coordinate position of the detector 37 has been changed.

In a camera or detector/determiner system where the camera position provides the fixed reference, rather than trackable reference fixture 35, very slight movements in the detector mounting can have a significant effect on the accuracy of the system. Because the position of the trackable reference fixture 35 with respect to the three-dimensional coordinate position of the body 61 of the detector 37 can be readily determined by the determiner 39, once the transform matrix M has been determined, the three-dimensional coordinate position of the body 61 of the detector 37 need not remain in a highly stable position. That is, the detector 37 can be readily moved without losing reference to the isocenter 43 because, rather than the detector 37 performing the function of a reference fixture, the trackable reference fixture 35 provides a relative fixed reference to the isocenter 43. Further, having a reference fixture, especially one positioned close to the isocenter 43 provides additional significant advantages. The greater the distance between the reference fixture and the isocenter 43, the less accurate the system. Still further, advantageously, the trackable reference fixture 35 allows the detector 37 to be positioned in a less intrusive location and with a less stable mounting than would otherwise be required.

In an embodiment of the present invention, the trackable reference fixture 35 can be used in place of trackable body 33 on at least one of the rotating assemblies. In the linear accelerator example, this feature allows the trackable reference fixture 35 to be and remain continuously connected to the gantry head 57 of the rotating gantry assembly 51. Further, advantageously, a trackable body 33 can be positioned or remain on the treatment table assembly 55 so as to allow the determiner 39 to help a therapist rotate the treatment table assembly 55 to position the target T in the proper juxtaposition with the isocenter 43.

Figure 8:
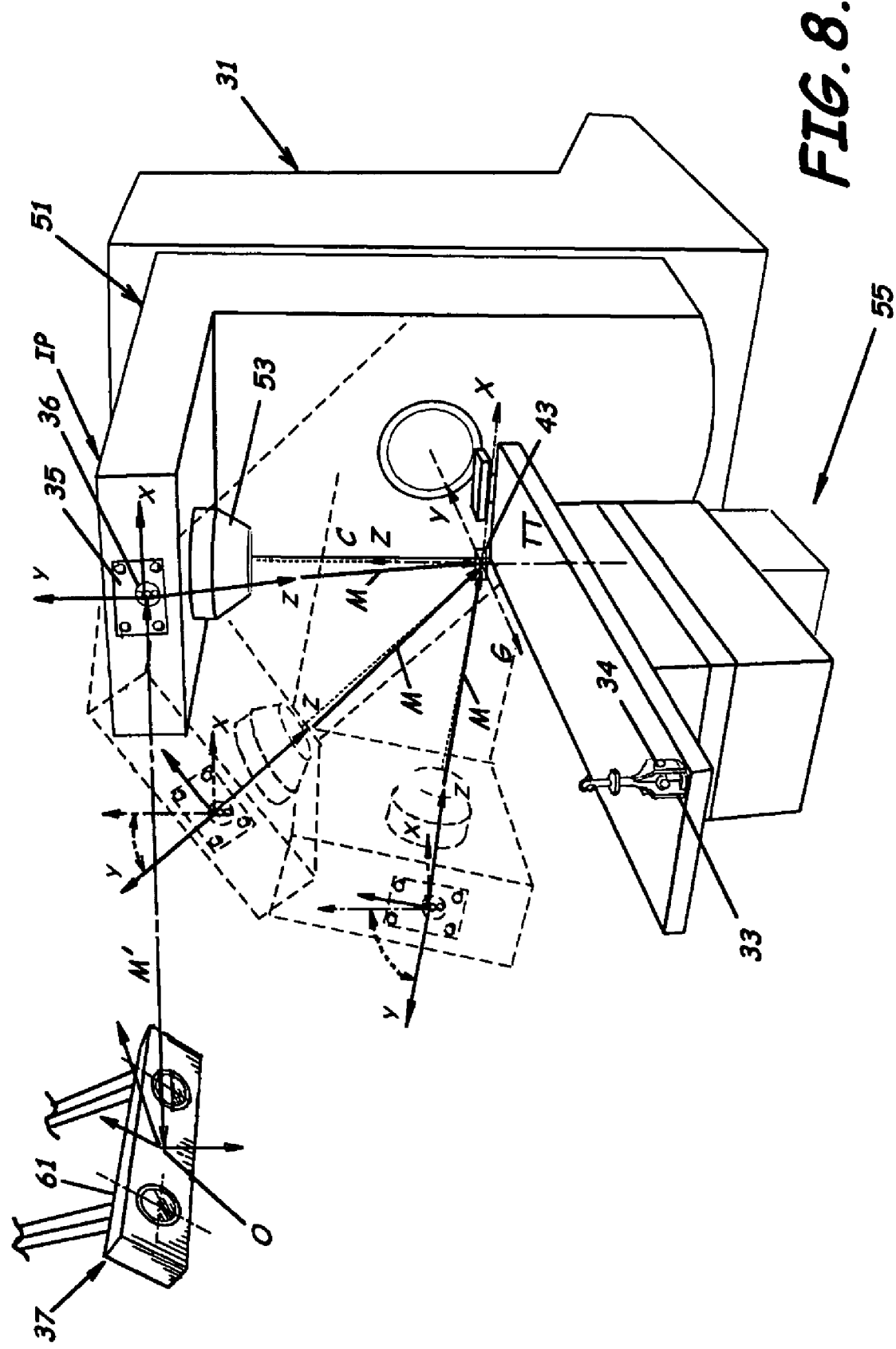
FIG. 8 is a perspective view of a system to analyze a geometry of a radiation treatment apparatus illustrating the determination of an isocenter of a treatment apparatus according to an embodiment of the present invention.

As perhaps best shown in FIG. 8, when the trackable reference fixture 35 is connected to a rotating assembly, such as the rotating gantry assembly 51, it should be readily apparent that transform matrix M maintains a reference to the isocenter 43 that will appear to rotate with the rotation of the rotating gantry assembly 51. The isocenter 43 and corresponding isocenter coordinate system, however, remain stationary and do not rotate with the rotation of the rotating gantry assembly 51. The constant orientation trackable body 36, either part of the trackable reference fixture 35 (as illustrated) or separately connected to a preselected portion of the rotating gantry assembly 51, can provide a reference orientation which allows the determiner 39 to correct the reference orientation of the isocenter 43 provided by the trackable reference fixture 35 when the rotating gantry assembly 51 is rotated off its initial reference position IP. Thus, an accurate reference position and orientation of the isocenter 43 can be provided (determined) regardless of the rotational orientation of the trackable reference fixture 35, due to rotation of the rotating gantry assembly 51. As shown in FIG. 1, similar to the trackable body or bodies 33, the constant orientation trackable body 36 includes a plurality of indicators, such as indicators 34, to allow position detection by a suitable detector, such as detector 37, and position and orientation determination of the trackable reference fixture by a suitable determiner, such as determiner 39. Rather than being fixedly mounted, the constant orientation trackable body 36 is preferably of a pendulum-type which can be pivotally connected to either a rotating assembly, such as the rotating gantry assembly 51, or to the trackable reference fixture 35, itself. The constant orientation trackable body 36 can be appropriately weighted and dampened to maintain the constant orientation during rotation of the rotating gantry assembly 51.

In this preferred embodiment of the present invention, the plurality of indicators 34 for the trackable reference fixture 35 and the constant orientation trackable body 36 are positioned on the respective fixture 35 and body 36 so that they have unique segment lengths between each other. This allows the detector 37/determiner 39 to uniquely identify the trackable reference fixture 35 and constant orientation trackable body 36 when viewed by the detector 37. As such, the plurality of indicators 34 of the respective trackable reference fixture 35 and constant orientation trackable body 36 are positioned with respect to a selected origin of a coordinate system assigned to or preselected for the respective trackable reference fixture 35 and constant orientation trackable body 36. This allows the determiner 39 to determine a three-dimensional coordinate position for the origin and linear direction of the each axes of the coordinate system separately assigned to or preselected for the trackable reference fixture 35 and constant orientation trackable body 36. Note, in this preferred embodiment of the present invention, the linear direction of the axes of the coordinate system assigned to or preselected for the trackable reference fixture 35 define a trackable reference fixture orientation that varies during rotation of the rotating gantry assembly 51. Other methodologies of defining orientation, however, known by those skilled in the art are within the scope of the present invention. For example, orientation could be defined as the longitudinal, lateral, or some other real or user-defined axes of the trackable reference fixture 35, which correspondingly also vary by an proportional amount during rotation of the rotating gantry assembly 51.

Figure 6:
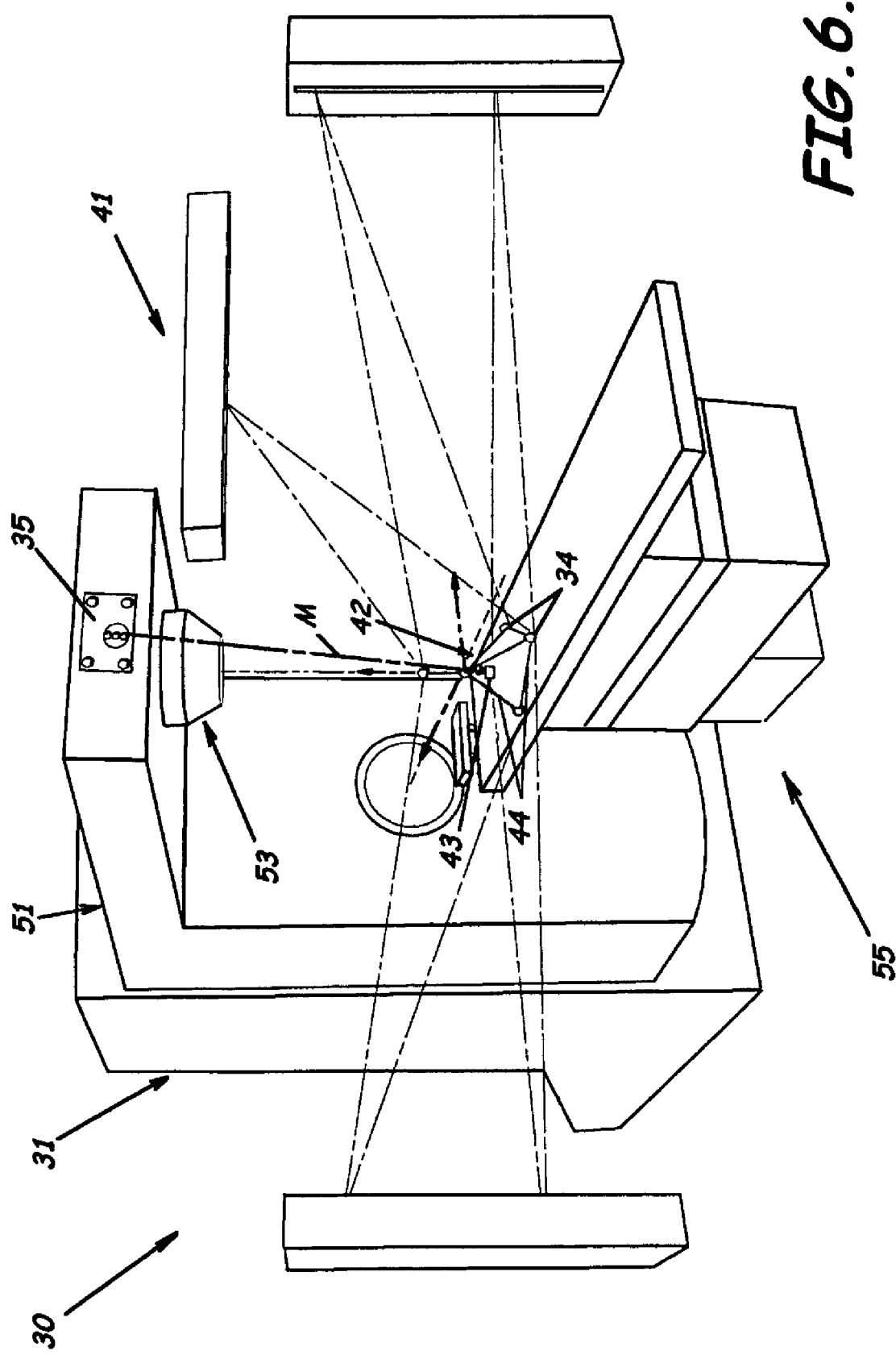
FIG. 6 is a perspective view of a laser array according to an embodiment of the present invention.
Figure 7:
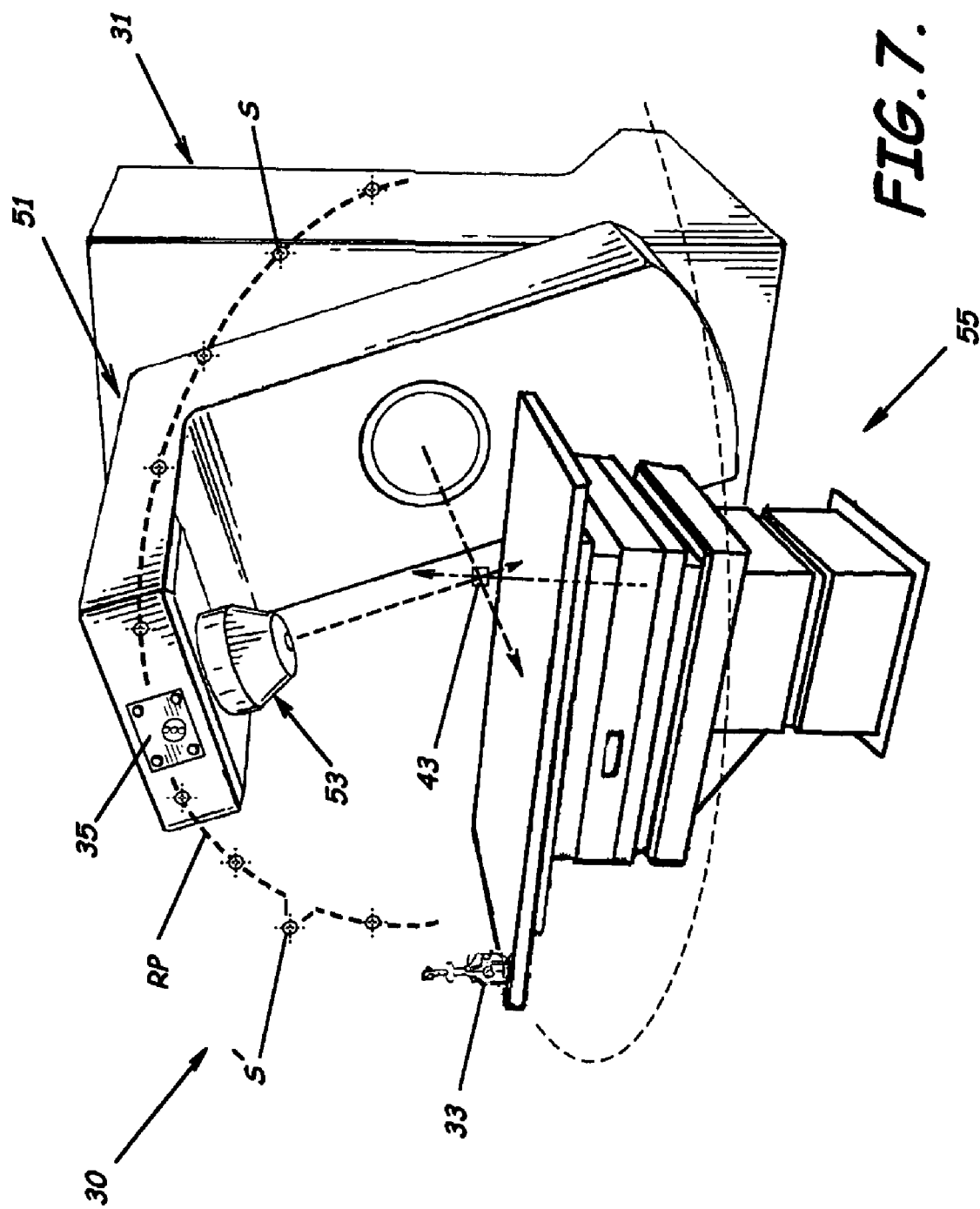
FIG. 7 is a perspective view of a treatment apparatus similar to that shown in FIG. 3 illustrating a rotational path of a rotating assembly having imperfections according to an embodiment of the present invention.

As perhaps best shown in FIG. 6, the system 30 can further include a laser array 41. Laser arrays are known and are used to calibrate camera locator-type systems to the isocenter of a radiation treatment apparatus. In an embodiment of the present invention, however, laser array 41 is not required to calibrate such a camera locator system or detector 37. Instead, the trackable reference fixture 35 and predetermined offset matrix M, which identifies to the detector 37/determiner 39 the position and/or orientation of the isocenter 43, can be used in conjunction with a trackable laser alignment body 42, having either alignment markings (not shown) or alignment edges 44, and indicators such as indicators 34, to align the laser arrays 41. Once the trackable laser alignment body 42 is positioned in view of the detector 37 to provide an operator a physical indication of the location of the isocenter 43, the respective lasers forming the laser array 41 can then be aligned to the alignment edges 44. Thereafter, a laser array 41 provides a visual indication of the three-dimensional coordinate position for the isocenter 43, which can be used for patient (target) positioning. Note, although shown in a unique geometric form, laser alignment body 42 take the form of other geometric shapes. That is, the laser alignment body 42 can be, but is not limited to being spherically shaped, cylindrically shaped, conically shaped, and cubically shaped.

Figure 2:
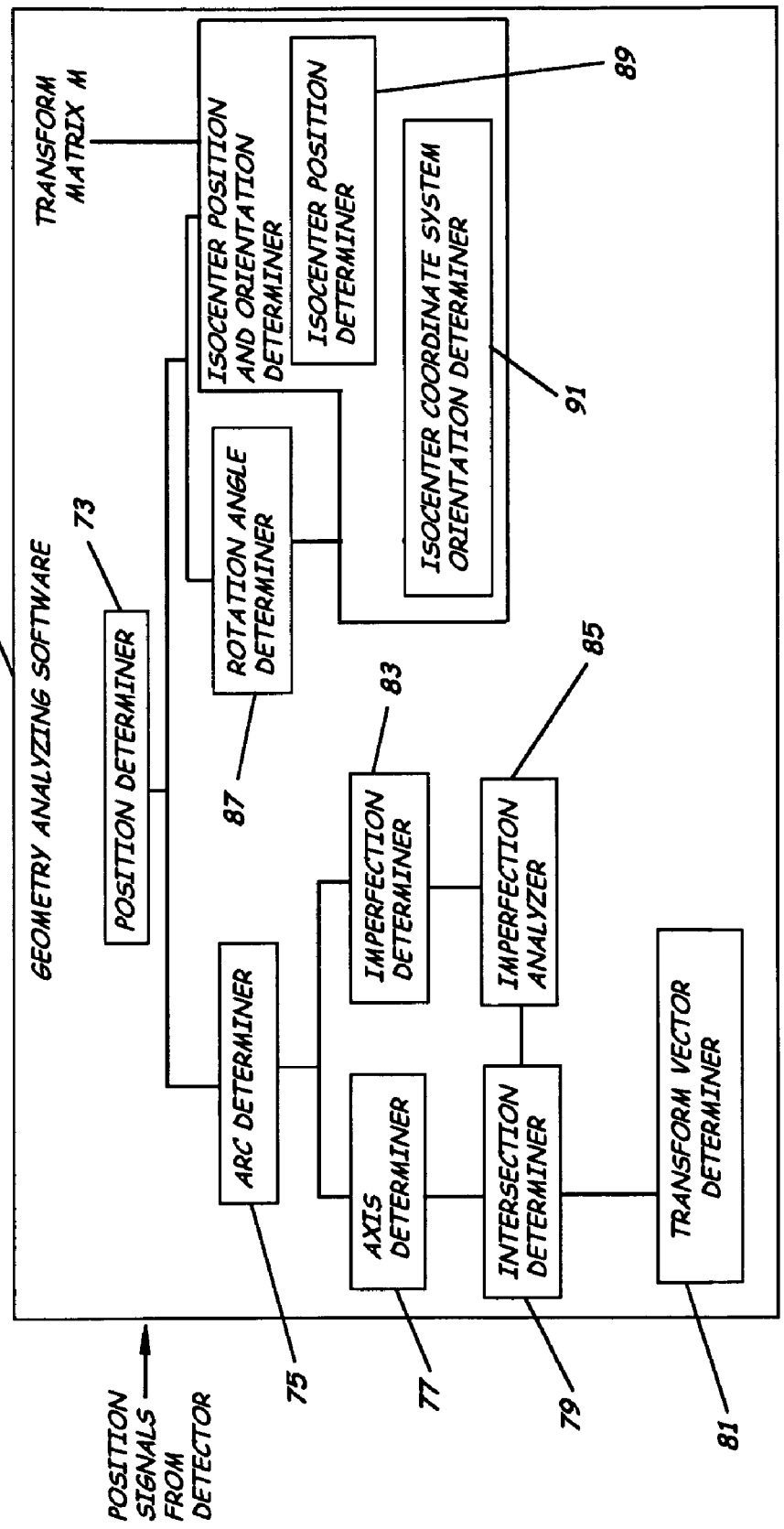
FIG. 2 is a schematic diagram of software to analyze a geometry of a radiation treatment apparatus according to an embodiment of the present invention.

As shown in FIG. 2 and as stated previously, in the preferred embodiment of the present invention, the determiner 39 includes geometry analyzing software 71 to analyze the geometry of the radiation treatment apparatus, illustrated as linear accelerator 31. The geometry analyzing software 71 includes a position determiner 73 adapted to receive a plurality of position signals from a detector such as detector 37. The position signals indicate the position of at least a subset of the plurality of indicators 34 for each respective trackable body 33 (FIG. 3) in view of the detector 37 (FIG. 1). In the linear accelerator example, illustrated with respect to rotating assembly 51 (FIG. 3), only, the position determiner 73 utilizes the position signals to determine at least two but preferably three sets of three-dimensional coordinate sampled data points or positions, such as positions S for rotating assembly 51, with each set representing three-dimensional coordinate sampled data points or positions located preferably substantially along the maximum rotational arc or path of a preselected portion of one of the rotating assemblies 51, 53, 55, such as, rotational path RP for rotating assembly 51. With appropriate filtering and smoothing, known and understood by those skilled in the art, an arc determiner 75 determines a fit of a separate arc A1, A2, A3 (FIGS. 3 and 4) for each set of three-dimensional coordinate sampled data points or positions S of the each rotating assembly 51, 53, 55. Correspondingly, each fitted arc A1, A2, A3, indicates the rotational path RP of the preselected portion of a respective one of the rotating assemblies 51, 53, 55, and is positioned in a plane substantially orthogonal to that of each other fitted arc. Note, though not all of the rotating assemblies are normally rotated throughout an entire 360 degrees of rotation, the fitted arcs A1, A2, A3, can nevertheless be represented either as true arcs (as illustrated by A1, A3) or as circles (as illustrated by A2) overlaid upon the three-dimensional coordinate sampled data points or positions, such as positions S for arc A1, representing the respective rotational paths.

An axis determiner 77, which may or may not be functionally separate from the arc determiner 75, can determine a center of rotation CR and normal N (FIG. 4) for each fitted arc A1, A2, A3. In the linear accelerator example, the center of rotation CR and normal N of the each fitted arc A1, A2, A3, correspondingly indicate the axes of rotation G, C, TT (FIG. 1) of each of the rotating assemblies 51, 53, 55. Further, an intersection determiner 79 determines an intersection I (FIG. 4) of the normals N indicating the intersection of the axes of rotation G, C, TT, of the respective rotating assemblies 51, 53, 55. The intersection I substantially indicates the three-dimensional coordinate position of the isocenter 43 of the isocenter coordinate system. Note, as stated above, in the linear accelerator example, only two of the rotating assemblies 51, 53, 55, need be sampled because the intersection I can be formed with two normals N, however, sampling coordinates from the rotational path of each of the primary rotating assemblies (rotating assemblies 51, 53, 55, for the linear accelerator 31), provides added data useful to form a more accurate determination of the isocenter 43. Note also, where the apparatus includes only a single rotating assembly, the center and normal requires more complicated mathematical algorithms and, although within the scope of the present invention, generally does not provide the accuracy of that provided by determining an intersection of two or more rotating assemblies.

When the trackable fixture 35 is fixedly connected to a rotating assembly, it can provide a reference to the determined three-dimensional coordinate position an orientation of the isocenter 43. That is, the geometry analyzing software 71 can include a transform matrix determiner 81 which can utilize the determined three-dimensional coordinate position of the isocenter 43 to determine a transform matrix M between the determined three-dimensional coordinate position of the isocenter 43 of the apparatus (e.g. linear accelerator 31) and the trackable fixture 35. This advantageously allows the body 61 of the detector 37 to be moved without losing reference to the three-dimensional coordinate position of the isocenter 43. More specifically, the position determiner 73 can also receive position signals indicating the three-dimensional coordinate position and/or orientation of a reference fixture, such as the trackable reference fixture 35. Having such three-dimensional coordinate position of the trackable reference fixture 35 and the determined three-dimensional coordinate position of the isocenter 43, the transform determiner 81 can determine the transform matrix M (see e.g. FIG. 5) between the determined three-dimensional coordinate position of the isocenter 43 and the trackable reference fixture 35. This transform matrix M allows a locator system, such as, detector 37/determiner 39, to readily determine a relative position and/or orientation of the isocenter 43 by merely viewing the trackable reference fixture 35 and determining the position and/or orientation of the trackable reference fixture 35.

In an embodiment of the present invention, the geometry software 71 also includes an imperfection identifier 83. The imperfection identifier 83 identifies if any of the three-dimensional sampled coordinate points or positions in either of the sets of three-dimensional coordinates are outside or not substantially coincident with three-dimensional coordinate points or positions in a dataset defining the respective fitted arc A1, A2, A3. Such three-dimensional coordinate points or positions, illustrated as position S' for the rotational path RP of the rotating assembly 51 (FIG. 7), when so determined, indicates a relative position of an imperfection in the respective rotating assembly 51, 53, 55. An imperfection analyzer 85 examines such imperfections to analyze an effect, if any, of the identified imperfections on the determined three-dimensional position of the isocenter 43 or on the isocenter coordinate system.

Advantageously, the geometry analyzing software 71 can directly determine (or re-determine) the three-dimensional coordinate position of the isocenter 43 and the orientation of the isocenter coordinate system utilizing a reference fixture, such as trackable reference fixture 35, and the predetermined transform matrix M stored in memory 69 which indicates a magnitude and a direction between the trackable reference fixture 35 and the isocenter 43. For example, in an embodiment of the present invention, a position determiner, such as position determiner 73, can receive a plurality of position signals formed by detecting a position of a plurality of indicators 34 on a trackable reference fixture, such as trackable reference fixture 35. That is, when the trackable reference fixture 35 is connected to one of the rotating assemblies, such as rotating gantry assembly 51 (FIG. 8), a position determiner 73 can be utilized to determine a position and/or orientation of the trackable reference fixture 35. An isocenter position determiner 89 can receive the determined position of the trackable reference fixture 35 and the predetermined matrix M to determine or re-determine the three-dimensional coordinate position and orientation of the isocenter 43 relative to the trackable reference fixture 35 to calibrate the detector 37/determiner 39 to the treatment apparatus.

Figure 5:
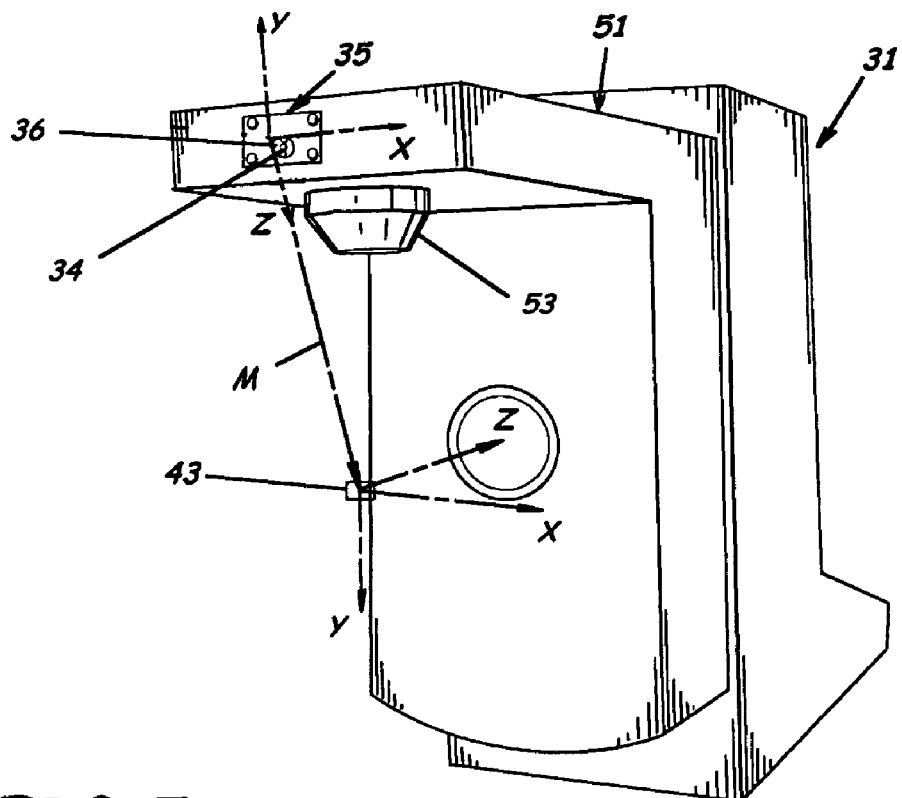
FIG. 5 is a perspective view of a treatment apparatus and a transform matrix between a trackable reference fixture and an isocenter of the treatment apparatus according to an embodiment of the present invention.

As described previously, the trackable reference fixture 35, being connected to a rotating assembly, such as, rotating assembly 51, by its nature has a variable orientation (FIG. 8) with respect to the orientation of the axis of the isocenter coordinate system, which has a fixed orientation (see FIGS. 5 and 8). In an embodiment of the present invention, the position determiner 73 can receive a first plurality of position signals to determine a position and an orientation of the trackable fixture 35. A constant orientation trackable body 36 having an orientation that remains constant during rotation of the rotating assembly 51 can be connected to the rotating assembly 51 to compensate for an error in the determined orientation of the axis of the isocenter coordinate system caused by rotation of the trackable reference fixture 35 from an initial reference position IP, such as that illustrated in FIG. 8. The position determiner 73 can further receive a second plurality of position signals to determine a position and an orientation of a constant orientation trackable body 36. A rotation angle determiner 87, responsive to the position determiner 73, can determine an angular difference between the orientation of the trackable reference fixture 35 and the orientation of the constant orientation trackable body, which indicates an angle of rotation of the trackable reference fixture 35, and thus, an angle of rotation of the rotating assembly 51. This angle is then used by an isocenter coordinate system orientation determiner 91 to formulate a correction factor (angle) so that the isocenter coordinate system orientation determiner 91 can determine the correct orientation of the isocenter 43 with respect to the treatment apparatus, treatment room, and/or detector 37.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include: nonvolatile, hard-coded type media such as read only memories (ROMs) or erasable, electrically programmable read only memories (EEPROMs), recordable type media such as floppy disks, hard disk drives and CD-ROMs, and transmission type media such as digital and analog communication links.

As shown in FIGS. 1-11, embodiments of the present invention also include a computer readable medium that is readable by a computer to analyze the geometry of an apparatus having a plurality of rotating assemblies, such as, for example, the illustrated linear accelerator 31. For example, in an embodiment of the present invention, the computer readable medium comprises a set of instructions that, when executed by the computer, such as, for example, determiner 39, cause the computer to perform the operations of: receiving a plurality of position signals; and determining at least two but preferably three sets of three-dimensional coordinate sampled positions (e.g. positions S illustrated in FIG. 7) substantially located along a separate rotational path of a preselected portion of each of the respective rotating assemblies 51, 53, and/or 55. The instructions also include those for determining a fit of a separate arc A1, A2, and/or A3 (FIG. 4), to each of the respective sets of three-dimensional coordinate positions, responsive to the plurality of position signals. Each fitted arc A1, A2, and/or A3 indicates the rotational path of the preselected portion of one of the respective rotating assemblies 51, 53, and/or 55 and is positioned in a plane substantially orthogonal to that of each other fitted arc. The instructions also include those for determining a center of rotation CR and normal N (FIG. 4) for each fitted arc A1, A2, and/or A3 indicating the respective axes of rotation G, C, and/or TT, of each of the analyzed rotating assemblies 51, 53, and/or 55, and determining an intersection I of the axes of rotation G, C, and/or TT of the analyzed rotating assemblies 51, 53, and/or 55. The intersection I substantially indicates a three-dimensional coordinate position of an isocenter 43 of an isocenter coordinate system.

The instructions can also include those for determining a transform matrix M between the determined three-dimensional coordinate position of the isocenter 43 and a trackable reference fixture, such as trackable reference fixture 35 connected to one of the rotating assemblies. The instructions can further include those for identifying a three-dimensional coordinate position in a preselected one of the sets of three-dimensional coordinates, not substantially coincident with three-dimensional coordinate positions in a dataset defining the respective fitted arc (e.g. position S' illustrated in FIG. 7). Such three-dimensional coordinate position, when so determined, indicates a relative position of an imperfection in the respective rotating assembly. The instructions can still further include those for analyzing an effect from the identified imperfection, when so existing, on the determined three-dimensional position of the isocenter 43.

Also for example, and still with reference to the linear accelerator example, in an embodiment of the present invention the computer readable medium can comprise a set of instructions that, when executed by the computer, causes the computer to perform the operations of: receiving a first plurality of position signals, determining a position and an orientation of a variable orientation trackable reference fixture 35 connected to a rotating assembly 51, such as the rotating gantry assembly, receiving a second plurality of position signals, and determining a position and an orientation of a constant orientation trackable body 36 preferably connected to the rotating assembly 51. The instructions can also include those for determining an angular difference between the orientation of the variable orientation trackable fixture 35 and the orientation of the constant orientation trackable body 36. The angular difference indicates an angle of rotation of the variable orientation trackable reference fixture 35 and an angle of rotation of the rotating assembly 51. The instructions can also include those for performing the operations of retrieving from storage on the storage media (e.g. memory 69) a predetermined transform matrix M which indicates a magnitude, direction, and a rotation between the variable orientation trackable reference fixture 35 and the previously determined three-dimensional coordinate position of the isocenter 43, and determining a relative three-dimensional coordinate position and orientation of the isocenter 43 from the variable orientation trackable reference fixture 35. The instructions can also include those for performing the operation of determining an orientation of the isocenter coordinate system, responsive to orientation of the variable orientation trackable fixture 35 and the determined angular difference between the orientation of the variable orientation trackable fixture 35 and orientation of the constant orientation trackable body 36.

Figure 9:
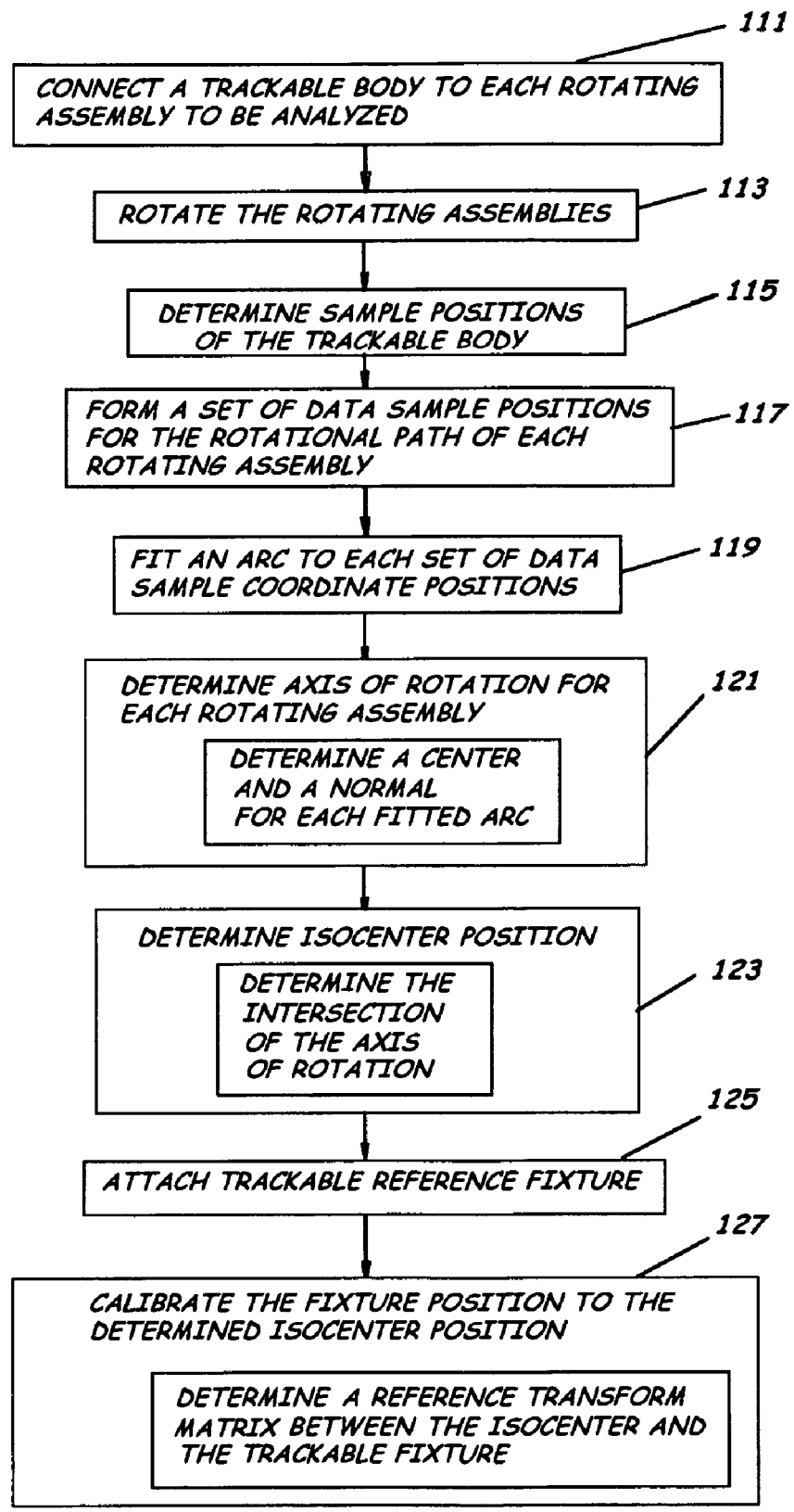
FIG. 9 is a flow chart of a method to analyze a geometry of a radiation treatment apparatus according to an embodiment of the present invention.
Figure 10:
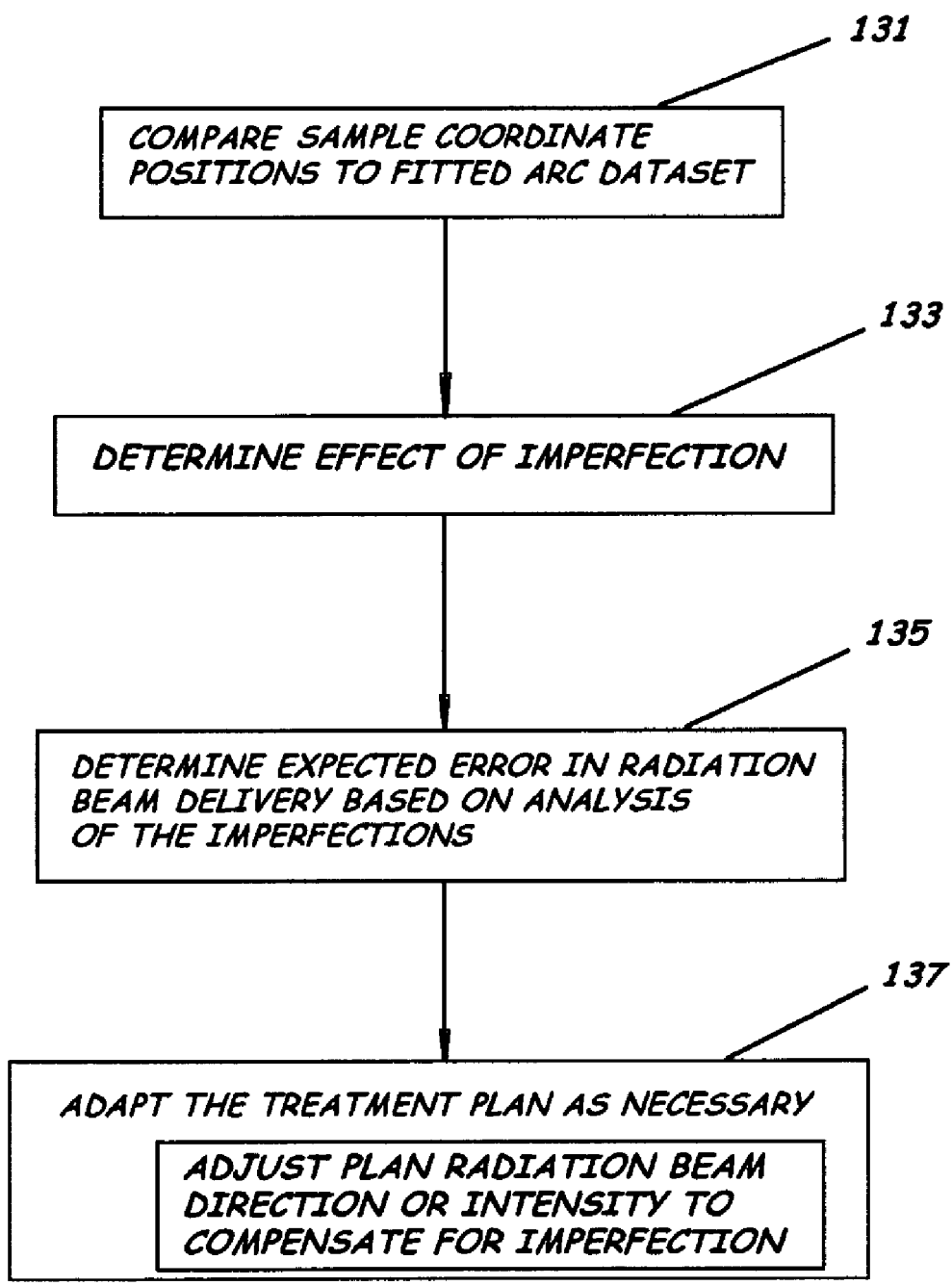
FIG. 10 is a flow chart of a method to analyze a geometry of a radiation treatment apparatus according to an embodiment of the present invention.

As shown in FIGS. 9-10, embodiments of the present invention also include methods for analyzing a geometry of an apparatus having a plurality of rotating assemblies, such as, the illustrated linear accelerator 31 (FIG. 1). As perhaps best shown in FIGS. 3 and 9, each respective rotating assembly 51, 53, 55, can have a trackable body, such as trackable body 33, connected either sequentially or simultaneously to each respective rotating assembly 51, 53, 55 (block 111), at a preselected portion of the respective rotating assembly 51, 53, 55. That is, in an embodiment of the present invention, a trackable body 33 can be sequentially connected to typically at least two but preferably three of the rotating assemblies 51, 53, 55, of the linear accelerator 31, for sequential viewing.

In another embodiment of the present invention, as illustrated in FIG. 3, each of a plurality of trackable bodies 33 can be individually and separately connected to a respective one of the rotating assemblies 51, 53, 55, for simultaneous viewing. Regardless, each rotating assembly 51, 53, 55, having a trackable body 33, connected thereto, can be rotated (block 113) by the user and viewed. A detector, such as detector 37, detects the position of a subset of the plurality of indicators 34 mounted to each trackable body 33 during rotation of the respective rotating assembly 51, 53, 55. The detector 37 produces a plurality of position signals indicative of the position of each of the subset of the plurality of indicators 34 in view of the detector 37. The plurality of position signals provide data which can be used by a determiner, such as determiner 39, to determine multiple sampled three-dimensional coordinate points or positions (block 115) in space along a rotational path of each respective rotating assembly 51, 53, 55, such as, for example sampled positions S along rotational path RP of the rotating assembly 51 illustrated in FIG. 3. The determiner 39 can further examine the position signals to categorize or form a separate set or sets of three-dimensional coordinate points or positions (block 117) along the rotational path of each of the rotating assemblies 51, 53, 55, being examined.

With use of appropriate filtering and smoothing, arcs A1, A2, A3 (FIGS. 3 and 4), which can extend to the circumference of a full circle, are each separately fitted (block 119) to a respective set of sampled data points or positions S for each corresponding rotating assembly 51, 53, 55. Each arc A1, A2, A3, has a center of rotation CR and a normal N extending from the center of rotation CR. This normal N defines the axis of rotation for each arc A1, A2, A3. Thus, the axis of rotation for each arc A1, A2, A3, can be readily determined (block 121). Correspondingly, in an embodiment of the present invention, the three-dimensional coordinate position of the isocenter 43 can be readily determined (block 123) by determining the intersection I of at least two but preferably all three of the axes of rotation G, C, TT, of the respective rotating assemblies 51, 53, 55, associated with the respective arcs A1, A2, A3.

Once the three-dimensional coordinate position of the isocenter 43 is determined, if not already installed, a trackable reference fixture 35 (FIG. 5) is connected or attached (block 125) to a preselected portion of preferably the most visible rotating assembly, the gantry head 57 of the rotating gantry assembly 51 for the linear accelerator 31. The three-dimensional coordinate position of the trackable reference fixture 35 can then be calibrated (block 127) to the determined three-dimensional coordinate position of the isocenter 43. This can be accomplished by determining a transform matrix M (FIG. 5) between the trackable reference fixture 35 and the determined three-dimensional coordinate position and assigned orientation of the isocenter 43. In the preferred embodiment of the present invention, determiner 39 accomplishes this function through use of software 71, described previously. Also, as stated previously, once the transform matrix M is determined, a trackable body locator or detector, such as detector 37, need not remain in a highly stable position. This provides a significant advantage as current camera locating systems are subject to wall vibrations and other movement. Rather than having the trackable body locator or detector perform the function of a reference fixture, the trackable reference fixture 35 provides the relative reference to the isocenter 43. Additionally, having a reference fixture positioned closer to the isocenter 43 even further advantageously improves accuracy.

As shown in FIG. 10, embodiments of the present invention also include methods for analyzing a geometry that include determining and analyzing imperfections of the geometry of the apparatus 31. For example, in an embodiment of the present invention, each fitted arc A1, A2, A3, (FIG. 4) can be considered to have its own dataset. That is, each respective fitted arc A1, A2, A3, is comprised of data points (three-dimensional coordinate positions) that fall along the curve defining the respective fitted arc A1, A2, A3. A comparison (block 131) can be made between at least one, but preferably all, of the three-dimensional coordinate sampled data points or positions (e.g. sampled data points S, FIG. 7) in each of the respective sets of the three-dimensional coordinate sampled data points or positions to three-dimensional coordinate positions in the respective datasets defining the respective fitted arc A1, A2, A3. Those points not considered to be substantially coincident, i.e., those that would not fall on the curve or dataset defining the respective fitted arc A1, A2, A3 (e.g. point S', FIG. 7), indicate a relative position of an imperfection in the respective rotating assembly 51, 53, 55.

Once a data point or points representing determined imperfections is found, an analysis or determination (block 133) can be made on an effect of the determined imperfection on the determined three-dimensional position of the isocenter 43 and on an orientation of the isocenter coordinate system. This analysis can include determining a relative rotational position of each determined imperfection utilizing the trackable reference fixture 35 and constant orientation trackable body 36. Further the analysis can also include a determination of an expected error (block 135) in, for example, radiation beam delivery. Advantageously, knowledge of the effects of such imperfections can allow the therapist to adapt a treatment plan (block 137), as necessary. In the linear accelerator example, this can be accomplished by adjusting the plan radiation beam direction or intensity to compensate for any such imperfections.

Figure 11:
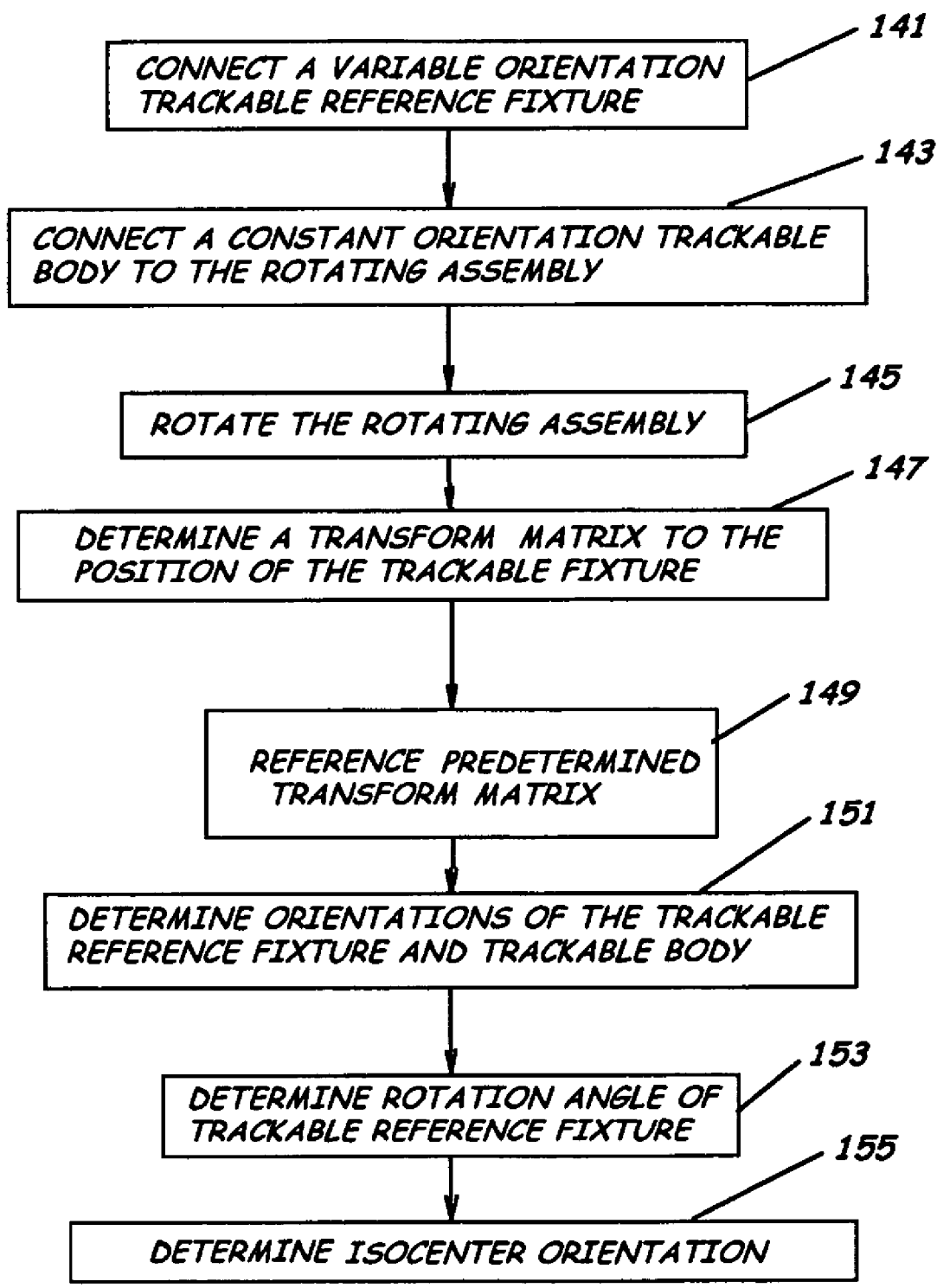
FIG. 11 is a flow chart of a method to analyze a geometry of a radiation treatment apparatus according to an embodiment of the present invention.

As perhaps best shown in FIG. 11, embodiments of the present invention also include methods for analyzing a geometry of a treatment apparatus 31 where a transform matrix M (FIG. 5) between a trackable reference fixture, such as trackable reference fixture 35, and a determined three-dimensional coordinate position and orientation of the isocenter 43, has already been predetermined. For example, in an embodiment of the present invention, a camera subsystem or suitable trackable body detector, such as detector 37, is positioned or optionally repositioned in a nonobstructive location. If not already done so, the trackable reference fixture 35 (FIG. 5) is connected to a rotating assembly (block 141) of the apparatus. For the illustrated linear accelerator 31, this rotating assembly preferably is the rotating gantry assembly 51. The trackable reference fixture 35 is preferably connected at the gantry head 57 (FIG. 5) to minimize the distance between the trackable reference fixture 35 and the determined isocenter 43. This positioning can help improve the accuracy of the system 30.

As perhaps best shown in FIGS. 8 and 11, in this configuration, however, because the rotating gantry assembly 51 rotates, the orientation of the trackable reference fixture 35 varies (rotates) with the rotation of the gantry head 57. As such, the predetermined offset matrix M will maintain a reference to the isocenter 43 that will rotate with the rotation of the rotating assembly 51 with respect to the linear accelerator 31, treatment room, and/or detector 37. The isocenter 43 and corresponding isocenter coordinate system, however, do not rotate with the rotation of the rotating assembly. Thus, a constant orientation trackable body 36 can be pivotally connected (block 143) on one end to either the trackable reference fixture 35 or separately connected directly to a preselected portion of the respective rotating assembly. The pendulum-type action of the constant orientation trackable body 36 provides a reference orientation which allows a determiner, such as determiner 39, to correct the orientation of the isocenter 43 provided by the trackable reference fixture 35 when the rotating assembly is rotated off its initial reference position. That is, the user can either intentionally or unintentionally rotate the rotating assembly 51 (block 145) and still obtain an accurate orientation of the isocenter coordinate system. Because the trackable reference fixture 35, provides a fixed reference to the three-dimensional coordinate position of the isocenter 43, the detector 37 can be readily moved without losing a ready reference to the isocenter 43, other than possibly temporarily during transit.

With the above described configuration, a very accurate three-dimensional coordinate position and orientation of the isocenter 43 can be readily transformed into detector/determiner (camera) space upon power-up of the detector 37/determiner 39. The detector 37 first detects a plurality of indicators 34 for the trackable reference fixture 35. With position signals produced therefrom, the determiner 39 then determines (block 147) a transform matrix V' (FIG. 8) between the detector 37 (e.g. detector position O) and the trackable reference fixture 35. Note, the detector 37 has a preselected coordinate system illustrated on the face of detector body 61. The preselected coordinate system, having a preselected origin and orientation, is established in a fixed relationship with the detector 37 to define a detector position O. Detector position O, however, is not a fixed coordinate reference position with respect to the treatment apparatus (e.g. linear accelerator 31) but moves with respect to the treatment apparatus correspondingly with movement of the detector body 61.

The determiner 39 then references the predetermined transform matrix M (block 149) to obtain a relative position and orientation of the isocenter 43. The detector 37 also detects a plurality of indicators 34 of the constant orientation trackable body 36. With position signals produced therefrom, the determiner 39 determines the orientation of the trackable reference fixture 35 and the constant orientation trackable body 39 (block 151). The determiner 39 can then determine the rotation angle of the trackable reference fixture 35 (block 153), which relates to the rotational position of the rotating assembly 51 from an initial reference position IP (FIG. 8). This can be accomplished by determining an angular difference between the trackable reference fixture 35 and the constant orientation trackable body 36. Conceptually, the determiner 39 determines the orientation of the isocenter 43 (block 155) by computationally rotating the relative orientation of the isocenter 43 obtained from the transform matrix M by an amount related to the angular difference between the trackable reference fixture 35 and the constant orientation trackable body 39 (see FIG. 8). Thus, an accurate reference position and orientation of the isocenter 43 is provided regardless of the rotational orientation of the trackable reference fixture 35, which can vary due to rotation of the rotating assembly for which the trackable reference fixture 35 is connected.

Advantageously, the above described steps can negate the need to use a laser array, such as, for example, laser array 41 (FIG. 6) to calibrate a camera subsystem/detector, such as, for example, detector 37. In fact, having determined the transform matrix M (FIG. 5), the laser array 41 can instead be aligned and calibrated by the detector 37. A preferably optically trackable laser alignment body 42 can be positioned at an offset coordinate position determined from the reference position of the trackable reference fixture 35 and the predetermined relative transform matrix M; a position coincident with the three-dimensional coordinate position for the isocenter 43. The laser array 41 can then be oriented upon the trackable laser alignment body 42 to allow alignment of the individual lasers of the laser array 41 to either alignment markings (not shown) or the alignment edges 44, and thus, to the three-dimensional coordinate position for the isocenter 43. This provides laser marking of the three-dimensional coordinate position for the isocenter 43 during patient positioning.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the attached claims. For example, the apparatus was described in the form of a linear accelerator. The invention, however, is not limited to apparatus that generate radiation and can be used with any apparatus having at least one rotating assembly, which requires analysis of the geometry of the apparatus to determine and analyze the coordinate system used by an operator. Also for example, the geometry analyzing software was generally described installed in the determiner, however, the software can be installed in the detector, in the determiner, in both, in a remote computer, or independently stored in a mobile storage media, such as, a compact disc, portable hard drive, etc. Further, the constant orientation trackable body was described as having a pendulum action. Other forms of action such as, for example, implementation of a gyroscope, are within the scope of the present invention.

The invention claimed is:

1. A system to analyze a geometry of a radiation treatment apparatus to determine a location of an origin and an orientation of a coordinate system used to reference radiation beam and patient positioning, the system comprising:
   a radiation treatment apparatus including a plurality of rotating assemblies each to direct a radiation beam through a target of a patient and each having a rotational path in a distinct plane and an axis of rotation, the axis of rotation of each rotating assembly intersecting the axis of rotation of each other rotating assembly of the plurality of rotating assemblies at a substantially same three-dimensional coordinate defining an isocenter of an isocenter coordinate system of the treatment apparatus;
   a plurality of optically trackable bodies, each connected to a preselected portion of a respective one of the plurality of rotating assemblies of the treatment apparatus, and each having a plurality of optical retro-reflective spheres mounted thereto;
   an optical detector having an optical detector body positioned spaced apart from the plurality of optically trackable bodies at a selected three-dimensional optical detector reference location and at least a pair of separate and spaced apart optical receivers connected to the optical detector body, each of the at least a pair of optical receivers positioned to receive optical energy reflected by a subset of the plurality of optical retro-reflective spheres of the optically trackable bodies to detect a three-dimensional sphere position of the plurality of retro-reflective spheres so that during rotation of the plurality of rotating assemblies the optical detector produces a plurality of position signals indicating three-dimensional coordinate positions for the plurality of optical retro-reflective spheres, and
   a determiner in communication with the optical detector to determine the isocenter of the radiation treatment apparatus, the determiner having memory associated therewith and geometry analyzing software stored in the memory to analyze radiation treatment apparatus geometry, the geometry analyzing software including:
      a position determiner responsive to the plurality of position signals from the optical detector to determine a respective set of three-dimensional coordinate positions for each one of the plurality of rotating assemblies, each set of three-dimensional coordinate positions located substantially along the rotational path of the preselected portion of each respective one of the plurality of rotating assemblies,
      an arc determiner responsive to the position determiner to determine a fit of a separate arc to each set of three-dimensional coordinate positions for each respective one of the plurality of rotating assemblies, each fitted arc indicating the rotational path of the preselected portion of a respective one of the plurality of rotating assemblies and positioned in a plane substantially orthogonal to that of each other fitted arc,
      an axis determiner responsive to the arc determiner to determine a center of rotation and a normal for each fitted arc indicating the axis of rotation of each respective one of the plurality of rotating assemblies, and
      an intersection determiner responsive to the axis determiner to determine an intersection of the axis of rotation of each of the plurality of rotating assemblies, the intersection substantially indicating the three-dimensional coordinate position of the isocenter.

2. A system as defined in claim 1, further comprising an optically trackable fixture fixedly connected to one of the plurality of rotating assemblies at a predetermined offset position relative to the determined three-dimensional coordinate position of the isocenter, and having a plurality of optical indicators mounted thereto having unique segment lengths between each of the plurality of optical indicators so that the determiner can identify the optically trackable fixture when viewed by the optical detector, and positioned with respect to an origin of a coordinate system preselected for the optically trackable fixture to determine a three-dimensional coordinate position for the origin and linear direction of the each axes of the assigned coordinate system of the optically trackable fixture, the linear direction of each axes of the preselected coordinate system of the optically trackable fixture defining an optically trackable fixture orientation that varies during rotation of the one of the plurality of rotating assemblies.

3. A system as defined in claim 2, further comprising:
an optically trackable laser alignment body adapted to be positioned at a predetermined offset position from the optically trackable fixture, the predetermined offset position coincident with the determined isocenter position, the optically trackable laser alignment body having a plurality of laser alignment markings to provide for laser alignment.

4. A system as defined in claim 3, further comprising:
a laser array adapted to be mounted in a fixed relationship to the radiation treatment apparatus and adapted to be oriented upon isocenter to allow alignment of lasers to the optically trackable laser alignment body to thereby provide laser marking of the determined isocenter position.

5. A system as defined in claim 1, wherein each set of three-dimensional coordinate positions for each respective one of the plurality of rotating assemblies are determined for a substantially maximum rotational arc of each of the plurality of rotating assemblies.

6. A system as defined in claim 5, wherein the geometry analyzing software further comprises:
an imperfection identifier, responsive to the arc determiner, to identify a three-dimensional coordinate position in the sets of three-dimensional coordinate not substantially coincident with three-dimensional coordinate positions in a dataset defining each respective fitted arc, such three-dimensional coordinate position, when so determined, indicating a relative position of an imperfection in the respective rotating assembly; and
an imperfection analyzer, responsive to the imperfection identifier, to analyze an effect from the identified imperfection, when so existing, on the determined three-dimensional position of the isocenter and on a determined orientation of the isocenter coordinate system.

7. A system as defined in claim 1, wherein a function of the plurality of optically trackable bodies is achieved through use of a single optically trackable body sequentially connected to the preselected portion of one of the plurality of rotating assemblies, separately rotated with the respective rotating assembly prior to connecting the optically trackable body to another one of the plurality of rotating assemblies, and viewed by the optical detector prior to connecting the optically trackable body to another one of the plurality of rotating assemblies.

8. A system as defined in claim 1, wherein the treatment apparatus comprises a linear accelerator including a rotating gantry assembly having a gantry axis of rotation, a gantry rotational outer circumference, a gantry head positioned adjacent the gantry rotational outer circumference to direct a radiation beam toward the gantry axis of rotation, a rotating beam collimator assembly connected to the gantry head and having a collimator axis of rotation positioned coaxially with a central axis of the radiation beam directed by the gantry head to shape the profile of the radiation beam, and a rotating patient treatment table having a treatment table axis of rotation and positioned adjacent the gantry assembly to move the position of the target of the patient with respect to the isocenter during treatment.

9. A system as defined in claim 8, further comprising an optically trackable fixture fixedly connected to the rotating gantry adjacent the gantry rotational outer circumference and at a predetermined position relative to the determined three-dimensional coordinate position of the isocenter, and wherein the optically trackable fixture is a suitable substitute for one of the plurality of optically trackable bodies.

10. A system as defined in claim 9, further comprising a constant orientation optically trackable body connected to the rotating gantry and having an orientation that remains constant during rotation of the rotating gantry to provide the determiner a reference orientation, to thereby determine an angle of rotation of the rotating gantry assembly.

11. A system to analyze a geometry of an apparatus, the system comprising:
an apparatus including a plurality of rotating assemblies each having a rotational path in a distinct plane and an axis of rotation, the axis of rotation of each rotating assembly intersecting the axis of rotation of each other rotating assembly of the plurality of rotating assemblies at a substantially same three-dimensional coordinate defining an isocenter of the apparatus;
a trackable body connected to a preselected portion of one of the plurality of rotating assemblies of the apparatus and having a plurality of indicators mounted thereto;
a detector having a detector body positioned spaced apart from the trackable body and a receiver positioned to receive energy from the plurality of indicators of the trackable body to detect a three-dimensional indicator position of the plurality of indicators so that during rotation of the one of the plurality of rotating assemblies the detector produces a plurality of position signals indicating the three-dimensional indicator position of the plurality of indicators; and
a determiner in communication with the detector and responsive to the plurality of position signals produced by the detector during rotation of the one of the plurality of rotating assemblies to determine a set of three-dimensional coordinate positions for the preselected portion of the one of the plurality of rotating assemblies located substantially along the rotational path of the preselected portion of one of the plurality of rotating assemblies, to thereby determine the axis of rotation for the one of the plurality of rotating assemblies.

12. A system as defined in claim 11, wherein the determiner determines a separate set of three-dimensional coordinate positions of the preselected portion for each of at least two of the plurality of rotating assemblies, to thereby determine the axis of rotation for the at least two of the plurality of rotating assemblies and an intersection of the axis of rotation of the at least two of the plurality of rotating assemblies, the intersection substantially indicating the three-dimensional coordinate position of the isocenter.

13. A system as defined in claim 12, further comprising a trackable fixture fixedly connected to the one of the plurality of rotating assemblies at a predetermined offset position relative to the determined three-dimensional coordinate position of the isocenter, the trackable fixture having a plurality of indicators mounted thereto.

14. A system as defined in claim 13, further comprising a constant orientation trackable body connected to the one of the at least two of the plurality of rotating assemblies, having a plurality of indicators mounted thereto, and having an orientation that remains substantially constant during rotation of the one of the at least two of the plurality of rotating assemblies to provide a reference orientation.

15. A system as defined in claim 13, wherein the trackable body is sequentially connected to each preselected portion of the at least two of the plurality of rotating assemblies, separately rotated with each respective rotating assembly prior to connecting to another one of the at least two of the plurality of rotating assemblies, and viewed by the detector prior to connecting to another one of the at least two of the plurality of rotating assemblies, to provide the determiner additional position signals to determine the separate sets of three-dimensional coordinate positions for the preselected portion of each of the at least two of the plurality of rotating assemblies.

16. A system as defined in claim 12,
    wherein the determiner has memory and geometry analyzing software stored in the memory to analyze apparatus geometry; and
    wherein the geometry analyzing software further comprises:
        a position determiner responsive to the plurality of position signals from the detector to determine the respective sets of three-dimensional coordinate positions for the at least two of the plurality of rotating assemblies; and
        an arc determiner responsive to the position determiner to determine a fit of a separate arc to each set of three-dimensional coordinate positions, each fitted arc indicating the rotational path of the preselected portion of one of the at least two of the plurality of rotating assemblies and positioned in a plane substantially orthogonal to that of the other fitted arc.

17. A system as defined in claim 16, wherein the geometry analyzing software further comprises:
    an axis determiner responsive to the arc determiner to determine a center of rotation and a normal for each fitted arc separately indicating the axis of rotation of each of the at least two of the plurality of rotating assemblies; and
    an intersection determiner responsive to the axis determiner to determine an intersection of the axes of rotation of the at least two of the plurality of rotating assemblies, the intersection substantially indicating the three-dimensional coordinate position of the isocenter.

18. A system as defined in claim 17,
    wherein each set of three-dimensional coordinate positions for each respective one of the at least two of the plurality of rotating assemblies are determined for a substantially maximum rotational are of each of the at least two of the plurality of rotating assemblies; and
    wherein the geometry analyzing software further comprises:
        an imperfection identifier, responsive to the arc determiner, to identify a three-dimensional coordinate position in the sets of three-dimensional coordinate positions not substantially coincident with three-dimensional coordinate positions in a dataset defining each respective fitted arc, such three-dimensional coordinate position, when so identified, indicating a relative position of an imperfection in the respective rotating assembly, and
        an imperfection analyzer, responsive to the imperfection identifier, to analyze an effect from the identified imperfection on the determined three-dimensional position of the isocenter, when so existing.

19. A system as defined in claim 11, wherein the one of the plurality of rotating assemblies is a first one of the plurality of rotating assemblies, wherein the trackable body is a first trackable body connected to the preselected portion of the first one of the plurality of rotating assemblies, wherein the system further comprises a second trackable body connected to the preselected portion of a second one of the plurality of rotating assemblies and having a plurality of indicators mounted thereto, wherein the detector receiver is positioned to receive energy from the plurality of indicators of the second trackable body to detect a three-dimensional indicator position of the plurality of indicators so that during rotation of the second of the plurality of rotating assemblies the detector produces a plurality of position signals indicating the three-dimensional indicator position of the plurality of indicators of the second trackable body, and wherein the determiner determines a second set of three-dimensional coordinate positions for the preselected portion of the second one of the plurality of rotating assemblies, to thereby determine the axis of rotation for the second one of the plurality of rotating assemblies and the intersection of the axes of rotation of the first one and the second one of the plurality of rotating assemblies, the intersection substantially indicating the three-dimensional coordinate position of the isocenter.

20. A system as defined in claim 11,
    wherein the determiner determines a separate set of three-dimensional coordinate positions for the preselected portion of each of the plurality of rotating assemblies, to thereby determine the axis of rotation for each respective rotating assembly and an intersection of the axis of rotation of each of the plurality of rotating assemblies, the intersection substantially indicating the three-dimensional coordinate position of the isocenter;
    wherein the apparatus comprises a linear accelerator including a rotating gantry assembly having a gantry axis of rotation, a gantry rotational outer circumference, and a gantry head positioned adjacent the gantry rotational outer circumference to direct a radiation beam toward the gantry axis of rotation, a rotating beam collimator assembly connected to the gantry head and having a collimator axis of rotation positioned coaxially with a central axis of the radiation beam directed by the gantry head to shape the profile of the radiation beam, and a rotating patient treatment table having a treatment table axis of rotation and positioned adjacent the gantry assembly to move the position of the target of the patient with respect to the isocenter during treatment; and
    wherein the system further comprises a trackable fixture adapted to the fixedly connected to the rotating gantry adjacent the gantry rotational outer circumference and at a predetermined offset position and orientation relative to the determined three-dimensional coordinate position of the isocenter, the trackable fixture having a plurality of indicators mounted thereto.

21. Geometry analyzing software stored on a storage media to analyze geometry of an apparatus having a plurality of rotating assemblies, the geometry analyzing software including:
    a position determiner adapted to receive a plurality of position signals to determine at least two sets of three-dimensional coordinate positions substantially located along a separate rotational path of a preselected portion of a respective at least two rotating assemblies of the apparatus; and an arc determiner responsive to the position determiner to determine a fit of a separate arc to each of the at least two sets of three-dimensional coordinate positions, each fitted arc indicating the rotational path of the preselected portion of one of the at least two rotating assemblies and positioned in a plane substantially orthogonal to that of each other fitted arc.

22. Software as defined in claim 21, wherein the geometry analyzing software further comprises:
an axis determiner responsive to the arc determiner to determine a center of rotation and a normal for each fitted arc indicating the respective axes of rotation of each of the at least two rotating assemblies; and
an intersection determiner responsive to the axis determiner to determine an intersection of the axes of rotation of the at least two rotating assemblies, the intersection substantially indicating a three-dimensional coordinate position of an isocenter of an isocenter coordinate system.

23. Software as defined in claim 22, further comprising a transform determiner responsive to the intersection determiner to determine a transform matrix between the determined three-dimensional coordinate position of the isocenter of the apparatus and a trackable fixture when fixedly connected to one of the at least two rotating assemblies.

24. Software as defined in claim 22, wherein each set of three-dimensional coordinate positions for each respective one of the at least two rotating assemblies are determined for a substantially maximum rotational arc of each of the at least two rotating assemblies.

25. Software as defined in claim 24, wherein the software further comprises an imperfection identifier, responsive to the arc determiner, to identify a three-dimensional coordinate position in a preselected one of the at least two sets of three-dimensional coordinates, not substantially coincident with three-dimensional coordinate positions in a dataset defining the respective fitted arc, such three-dimensional coordinate position, when so identified, indicating a relative position of an imperfection in the respective rotating assembly.

26. Software as defined in claim 25, wherein the software further comprises an imperfection analyzer, responsive to the imperfection identifier, to analyze an effect from the identified imperfection, when so existing, on the determined three-dimensional position of the isocenter.

27. Geometry analyzing software stored on a storage media to analyze geometry of an apparatus having a plurality of rotating assemblies, the geometry analyzing software including:
a position determiner adapted to receive a first plurality of position signals, to determine a position and an orientation of a variable orientation trackable reference fixture connected to a rotating assembly of the apparatus, the variable orientation trackable reference fixture having an orientation that varies during rotation of the rotating assembly, and adapted to receive a second plurality of position signals, to determine a position and an orientation of a constant orientation trackable body connected to the rotating assembly of the apparatus, the constant orientation trackable body having an orientation that remains constant during rotation of the rotating assembly; and
a rotation angle determiner, responsive to the position determiner to determine an angular difference between the orientation of the variable orientation trackable fixture and the orientation of the constant orientation trackable body, the angular difference indicating an angle of rotation of the variable orientation trackable reference fixture and an angle of rotation of the rotating assembly.

28. Software as defined in claim 27, wherein a predetermined transform matrix is stored on the storage media, the predetermined transform matrix indicating a magnitude and a direction between the variable orientation trackable reference fixture and a predetermined isocenter of the apparatus.

29. Software as defined in claim 28, wherein the software further comprises an isocenter position determiner, responsive to the position determiner and positioned to receive the predetermined transform matrix from the storage media, to determine a relative position of the isocenter from the variable orientation trackable reference fixture.

30. Software as defined in claim 29, wherein the software further comprises an isocenter coordinate system orientation determiner responsive to the rotation angle determiner and isocenter position determiner to determine an orientation of the isocenter coordinate system.

31. A computer readable medium that is readable by a computer to analyze geometry of an apparatus having a plurality of rotating assemblies, the computer readable medium comprising a set of instructions stored thereon that, when executed by the computer, cause the computer to perform the following operations:
receiving a plurality of position signals;
responsive to the plurality of position signals, determining at least two sets of three-dimensional coordinate positions substantially located along a separate rotational path of a preselected portion of a respective at least two rotating assemblies of the apparatus;
determining a fit of a separate arc to each of the at least two sets of three-dimensional coordinate positions, each fitted arc indicating the rotational path of the preselected portion of one of the at least two rotating assemblies and positioned in a plane substantially orthogonal to that of each other fitted arc;
determining a center of rotation and a normal for each fitted arc indicating the respective axes of rotation of each of the at least two rotating assemblies; and
determining an intersection of the axes of rotation of the at least two rotating assemblies, the intersection substantially indicating a three-dimensional coordinate position of an isocenter of an isocenter coordinate system.

32. A computer readable medium as defined in claim 31, further comprising a set of instructions that, when executed by the computer, cause the computer to perform the following operation:
determining a transform matrix between the determined three-dimensional coordinate position of the isocenter of the apparatus and a trackable fixture when fixedly connected to one of the at least two rotating assemblies.

33. A computer readable medium as defined in claim 32, further comprising a set of instructions that, when executed by the computer, cause the computer to perform the following operation:
identifying a three-dimensional coordinate position in a preselected one of the at least two sets of three-dimensional coordinates, not substantially coincident with three-dimensional coordinate positions in a dataset defining the respective fitted arc, such three-dimensional coordinate position, when so determined, indicating a relative position of an imperfection in the respective rotating assembly; and
analyzing an effect from the identified imperfection, when so existing, on the determined three-dimensional position of the isocenter.

34. A computer readable medium that is readable by a computer to analyze geometry of an apparatus having a plurality of rotating assemblies, the computer readable medium comprising a set of instructions stored thereon that, when executed by the computer, cause the computer to perform the following operations:

receiving a first plurality of position signals;

determining a position and an orientation of a variable orientation trackable reference fixture connected to a rotating assembly of the apparatus, the variable orientation trackable reference fixture having an orientation that varies during rotation of the rotating assembly;

receiving a second plurality of position signals;

determining a position and an orientation of a constant orientation trackable body connected to the rotating assembly of the apparatus, the constant orientation trackable body having an orientation that remains constant during rotation of the rotating assembly; and determining an angular difference between the orientation of the variable orientation trackable fixture and the orientation of the constant orientation trackable body, the angular difference indicating an angle of rotation of the variable orientation trackable reference fixture and an angle of rotation of the rotating assembly.

35. A computer readable medium as defined in claim 34, further comprising a set of instructions that, when executed by the computer, cause the computer to perform the following operations:

retrieving a predetermined transform matrix stored on the computer readable media, the predetermined transform matrix indicating a magnitude and a direction between the variable orientation trackable reference fixture and a predetermined isocenter of the apparatus; and determining a relative position of the isocenter from the variable orientation trackable reference fixture, responsive to the determined position of the variable orientation trackable body and the predetermined transform matrix.

36. A computer readable medium as defined in claim 35, further comprising a set of instructions that, when executed by the computer, cause the computer to perform the following operation:

determining an orientation of the isocenter coordinate system, responsive to orientation of the variable orientation trackable fixture and the determined angular difference between the orientation of the variable orientation trackable fixture and the orientation of the constant orientation trackable body.

37. A method for analyzing a geometry of an apparatus including a plurality of rotating assemblies each having an optically trackable body connected to a preselected portion of each respective rotating assembly, the method comprising the steps of:

determining at least two sets of three-dimensional coordinate positions in space substantially along at least a portion of a separate rotational path of the preselected portion of each of a respective at least two rotating assemblies of the apparatus; and determining a fit of a separate arc to each of the at least two sets of three-dimensional coordinate positions, each fitted arc indicating the rotational path of the preselected portion of one of the at least two rotating assemblies.

38. A method as defined in claim 37, further comprising the steps of:

determining a center of rotation and a normal for each fitted arc indicating the axis of rotation of each of the at least two rotating assemblies; and determining an intersection of the axes of rotation of the at least two rotating assemblies, the intersection substantially indicating a three-dimensional coordinate position of an isocenter of an isocenter coordinate system.

39. A method as defined in claim 38, further comprising the steps of:

connecting a trackable fixture to one of the at least two rotating assemblies, the fixture providing a fixed reference distance and direction to the determined three-dimensional coordinate position of the isocenter; and determining a transform matrix between the determined three-dimensional coordinate position of the isocenter of the apparatus and the trackable fixture, the transform matrix providing a reference to the determined three-dimensional coordinate position of the isocenter.

40. A method as defined in claim 38, wherein the step of determining at least two sets of three-dimensional coordinate positions in space includes the step of determining the set of three-dimensional coordinate positions of one of the at least two rotating assemblies for a substantially maximum rotational arc.

41. A method as defined in claim 38, further comprising the step of:

determining three-dimensional coordinate positions, in a preselected one of the at least two sets of three-dimensional coordinates, not substantially coincident with three-dimensional coordinate positions in a dataset defining the respective fitted arc, such three-dimensional coordinate positions, when so determined, indicating a relative position of an imperfection in the respective rotating assembly.

42. A method as defined in claim 41, further comprising the step of:

analyzing an effect on a predetermined three-dimensional position and orientation of an isocenter of an isocenter coordinate system from the determined imperfections, when so existing, to thereby adapt a radiation treatment plan responsive to the analyzed effect of the determined imperfections.

43. A method as defined in claim 42, wherein the step of analyzing an effect on the determined three-dimensional position of the isocenter includes the step of determining a relative rotational position of each determined imperfection, to thereby adapt the radiation treatment plan to vary a planned radiation beam intensity or direction responsive to the determined relative rotational position of each determined imperfection.

44. A method for analyzing a geometry of an apparatus having a rotating assembly, the method comprising the steps of:

connecting a trackable fixture to a rotating assembly at a predetermined three-dimensional trackable fixture coordinate position, the trackable fixture providing a fixed reference to a pre-determined three-dimensional coordinate position of an isocenter of an isocenter coordinate system;

determining a transform matrix between the predetermined three-dimensional trackable fixture coordinate position and the predetermined three-dimensional coordinate position of the isocenter; and determining the three-dimensional coordinate position of the isocenter of the isocenter coordinate system by determining a three-dimensional coordinate position of the trackable fixture at one of a plurality of three-dimensional coordinate positions located substantially along a rotational path of the rotating assembly and applying the transform matrix to the determined three-dimensional coordinate position of the trackable fixture.

45. A method for analyzing a geometry of an apparatus including a plurality of rotating assemblies, the method comprising the steps of:
forming at least two sets of three-dimensional coordinate positions, each set indicating a plurality of three-dimensional coordinate positions of at least a portion of a separate rotational path of a preselected portion of a respective at least two rotating assemblies of the radiation treatment apparatus, each preselected portion having a trackable body connected thereto;
determining an axis of rotation of each of the at least two rotating assemblies from the respective at least two sets of three-dimensional coordinate positions; and
determining an intersection of the axes of rotation of the at least two rotating assemblies, the intersection substantially indicating a three-dimensional coordinate position of an isocenter of an isocenter coordinate system.

46. A method as defined in claim 45, further comprising the step of:
connecting a trackable reference fixture to one of the at least two rotating assemblies, the fixture providing a fixed reference to the determined three-dimensional coordinate position of the isocenter.

47. A method as defined in claim 46, further comprising the step of:
determining a transform matrix between the three-dimensional coordinate position of the isocenter and a three-dimensional reference position of the trackable reference fixture.

48. A method as defined in claim 47, wherein the transform matrix is a first transform matrix, and wherein the method further comprises the step of:
determining a three-dimensional coordinate position of the trackable reference fixture to form a second transform matrix between a trackable body position detector three-dimensional coordinate position and the position of the trackable reference fixture to thereby form a three-dimensional reference to the determined three-dimensional coordinate position of the isocenter referenced to the trackable body position detector three-dimensional coordinate position.

49. A method as defined in claim 45, further comprising the step of:
determining, for one of at least two rotating assemblies, a relative position of an imperfection in the respective rotating assembly.

50. A method as defined in claim 49, wherein the three-dimensional coordinate position of the isocenter is used in the formulation of a treatment plan for a patient, and wherein the method further comprises the step of:
analyzing an effect on the three-dimensional position of the isocenter from the determined imperfection, when so existing, to thereby adapt the treatment plan responsive to the analyzed effect of the determined imperfection.

51. A method for analyzing a geometry of a treatment apparatus having a rotating assembly, the method comprising the steps of:
connecting a variable orientation trackable fixture to a rotating assembly of the treatment apparatus at a predetermined three-dimensional coordinate position, the variable orientation trackable fixture having an orientation that varies during rotation of the rotating assembly and a predetermined relative offset distance and relative direction to an isocenter of the treatment apparatus that does not vary during rotation of the rotating assembly; and
determining a three-dimensional coordinate position of the isocenter by detecting the three-dimensional coordinate position of the variable orientation trackable fixture.

52. A method as defined in claim 51, further comprising the step of:
connecting a constant orientation trackable body to the rotating assembly, the constant orientation trackable body having an orientation that remains substantially constant during rotation of the rotating assembly.

53. A method as defined in claim 52, further comprising the steps of:
determining an angular difference between the orientation of the variable orientation trackable fixture and the orientation of the constant orientation trackable body, the angular difference indicating a relative rotational position of the rotating assembly; and
determining an orientation of an isocenter coordinate system of the apparatus from a relative orientation of the variable orientation trackable fixture and the determined angular difference between the orientation of the variable orientation trackable fixture and the orientation of the constant orientation trackable body.

54. A method as defined in claim 51, further comprising the steps of:
positioning an optically trackable laser alignment body at a three-dimensional laser alignment coordinate position determined from a three-dimensional coordinate position of the trackable reference fixture and the predetermined relative offset distance and relative direction of the trackable reference fixture to the three-dimensional coordinate position of the isocenter, the three-dimensional laser alignment coordinate position substantially coincident with the three-dimensional coordinate position of the isocenter; and
positioning a laser array oriented upon the optically trackable laser alignment body to allow alignment of lasers to the three-dimensional coordinate position of the isocenter, to thereby provide laser marking of the determined three-dimensional coordinate position of the isocenter.

55. A method for analyzing a geometry of an apparatus comprising a rotating assembly having an optically trackable body connected at a preselected portion of the rotating assembly, the method comprising the steps of:
determining a set of three-dimensional coordinate positions substantially along at least a portion of a rotational path of a preselected portion of the rotating assembly of the apparatus;
determining a fit of an arc to the set of three-dimensional coordinate positions, the fitted arc indicating the rotational path of the preselected portion of the rotating assembly; and
determining a center of rotation for the fitted arc substantially indicating a three-dimensional coordinate position of an isocenter of an isocenter coordinate system.

56. A method as defined in claim 55,
wherein the optically trackable body is connected to a preselected portion of the rotating assembly;
wherein the optically trackable body has a plurality of separate and spaced-apart indicators each connected at a separate preselected position thereon to indicate to a trackable body position detector a separate three-dimensional coordinate position of each of the plurality of indicators; and wherein the step of determining a set of three-dimensional coordinate positions further comprises the steps of:
rotating the rotating assembly,
detecting, during rotation of the rotating assembly, a plurality of sets of indicator positions, each set of indicator positions indicating a three-dimensional coordinate position of the trackable body; and
determining a three-dimensional coordinate position of the trackable body for a subset of the plurality of sets of indicator positions.

57. A method as defined in claim 55, further comprising the step of:
connecting a trackable reference fixture to the rotating assembly, the trackable reference fixture providing a fixed reference distance and reference direction to the three-dimensional coordinate position of the isocenter.

58. A method as defined in claim 57, further comprising the step of: determining the three-dimensional coordinate position of the isocenter of the isocenter coordinate system by performing the steps of:
determining a distance and direction between a three-dimensional coordinate position of a trackable body position detector and a three-dimensional coordinate position of the trackable reference fixture when rotationally positioned at one of a plurality of three-dimensional coordinate positions located substantially along a rotational path of the rotating assembly, the distance and direction between the trackable body position detector and the trackable reference fixture defining a relative three-dimensional coordinate position of the trackable reference fixture;
applying a predetermined transform matrix to the relative three-dimensional coordinate position of the trackable reference fixture, the predetermined transform matrix having a magnitude and direction substantially related to the distance and the relative direction between the three-dimensional coordinate position of the trackable reference fixture and the three-dimensional coordinate position of the isocenter; and
wherein a fixed reference position of the trackable body detector is not required to determine the three-dimensional coordinate position of the isocenter when applying the predetermined transform matrix to the relative three-dimensional position of the trackable reference fixture to thereby determine three-dimensional coordinate position of the isocenter.

* * * * *